United States Patent
Tashino et al.

(10) Patent No.: US 6,770,586 B2
(45) Date of Patent: Aug. 3, 2004

(54) SOLID CATALYST COMPONENT AND CATALYST FOR OLEFINS POLYMERIZATION

(75) Inventors: Kunihiko Tashino, Kanagawa (JP); Yukihiro Suzuki, Kanagawa (JP); Isa Nishiyama, Kanagawa (JP); Hayashi Ogawa, Kanagawa (JP); Takuma Yoshida, Kanagawa (JP); Motoki Hosaka, Kanagawa (JP); Maki Sato, Kanagawa (JP)

(73) Assignee: Toho Titanium Co., Ltd., Chigasaki (JP)

( * ) Notice: Subject to any disclaimer, the term of this patent is extended or adjusted under 35 U.S.C. 154(b) by 0 days.

(21) Appl. No.: 10/018,857

(22) PCT Filed: Apr. 23, 2001

(86) PCT No.: PCT/JP01/03461

§ 371 (c)(1),
(2), (4) Date: Apr. 3, 2002

(87) PCT Pub. No.: WO01/81434

PCT Pub. Date: Nov. 1, 2001

(65) Prior Publication Data

US 2003/0130109 A1 Jul. 10, 2003

(30) Foreign Application Priority Data

Apr. 24, 2000 (JP) ........................................ 2000-122505
Aug. 30, 2000 (JP) ........................................ 2000-261620
Sep. 29, 2000 (JP) ........................................ 2000-298766

(51) Int. Cl.$^7$ .......................... B01J 31/00; B01J 37/00; C08F 4/02; C08F 4/60

(52) U.S. Cl. .................... 502/127; 502/125; 526/124.8; 526/125.4

(58) Field of Search ................................ 502/127, 125; 526/124.8, 125.4

(56) References Cited

U.S. PATENT DOCUMENTS

| | | | | |
|---|---|---|---|---|
| 4,547,476 A | * | 10/1985 | Terano et al. ................ | 502/127 |
| 4,970,186 A | * | 11/1990 | Terano et al. ................ | 502/125 |
| 4,985,515 A | * | 1/1991 | Matsuura et al. ......... | 526/124.8 |
| 5,354,820 A | * | 10/1994 | Funabashi ................. | 526/125.4 |
| 6,156,690 A | * | 12/2000 | Hosaka ........................ | 502/118 |
| 6,200,921 B1 | * | 3/2001 | Kataoka ...................... | 502/115 |
| 6,228,791 B1 | * | 5/2001 | Kataoka et al. ............. | 502/115 |
| 6,228,793 B1 | * | 5/2001 | Hosaka et al. .............. | 502/125 |
| 6,271,166 B1 | * | 8/2001 | Shinozaki et al. .......... | 502/126 |
| 6,323,150 B1 | * | 11/2001 | Kojoh et al. ................ | 502/125 |
| 6,429,270 B2 | * | 8/2002 | Morse .......................... | 526/118 |
| 6,521,560 B1 | * | 2/2003 | Kojoh et al. ................ | 502/104 |

FOREIGN PATENT DOCUMENTS

| | | |
|---|---|---|
| EP | 45977 | 2/1982 |
| EP | 601496 | 6/1994 |
| EP | 896969 | 2/1999 |
| WO | 00/08065 | 2/2000 |

OTHER PUBLICATIONS

Gerhard Staiger: "Modified titanium components for Ziegler–Natta catalyst systems". Chemical Abstracts, vol. 104, No. 8, abstract No. 51254 1986.

Gerhard Staiger: "Catalysts for the polymerization ofolefines." Chemical Abstracts, vol. 102, No. 22, abstract No. 185667 1985.

* cited by examiner

Primary Examiner—Mark L. Bell
Assistant Examiner—Jennine Brown
(74) Attorney, Agent, or Firm—Oblon, Spivak, McClelland, Maier & Neustadt, P.C.

(57) ABSTRACT

Solid catalyst components and catalysts which contain (a) magnesium compound, (b) titanium tetrachloride, and (c) a phthalic acid diester or its derivative are useful in the synthesis of olefin polymers in high yields. Particularly, propylene polymers can be obtain in very high yields while retaining high stereoregularity.

14 Claims, 1 Drawing Sheet

SOLID CATALYST COMPONENT AND CATALYST FOR OLEFINS POLYMERIZATION

TECHNICAL FIELD

The present invention relates to a solid catalyst component and catalyst for polymerization of olefins, which have a high responsiveness to hydrogen and can afford olefin polymers in very high yield while retaining high stereoregularity.

BACKGROUND ART

So far it has been known that some solid catalyst components used in polymerization of olefins contain magnesium, titanium, an electron donor compound and halogen as essential components. A large number of methods for olefin polymerization by polymerization or copolymerization of propylene, in the presence of a catalyst for olefin polymerization comprising the above solid catalyst components, an organoaluminum compound and organosilicon compound, have been proposed. For example, Japanese Unexamined Patent Publication No. (herein after referred to as JP-A) 57-63310/1982 and JP-A 57-63311/1982 disclose a method for polymerization of olefins of 3 carbon atoms or more, in which a combined catalyst comprising solid catalyst components containing a magnesium compound, titanium compound and an electron donor such as diester compound, e.g., phthalic acid ester, and an organoaluminum compound and an organosilicon compound having a Si—O—C linkage is used.

JP-A 1-6006/1989 discloses solid catalyst components for olefin polymerization, which contain a dialkoxymagnesium, titanium tetrachloride, and dibutyl phthalate, wherein propylene is somewhat effectively polymerized in the presence of the solid catalyst components to give a stereoregular polymer in high yield. In this situation, the polymers produced with the above catalysts have been utilized in various ways as molding products such as cars and household electric appliances as well as containers and films. In producing these products, polymer powder is melted and molded in anyone of various forming machines. Particularly, in producing large-sized molding products by means of injection molding, high fluidity (melt flow rate) of melted polymers is sometimes required, and many researches have been continued accordingly in order to enhance the melt flow rate of polymers.

The melt flow rate greatly depends on the molecular weight of polymers. In the polymer trade, it is general to add hydrogen as a molecular weight regulator for the polymer produced in polymerization of olefins. When low molecular weight polymers are produced, i.e., in order to produce polymers of high melt flow rate, a large quantity of hydrogen is usually added, though there is a limitation in a pressure reactor in terms of safety as well as in an adaptable amount of hydrogen. In order to add a much more amount of hydrogen, the partial pressure of monomer to be polymerized has to be decreased, but decrease of the partial pressure is accompanied by decrease of productivity. Additionally, use of a large amount of hydrogen may bring about a problem of cost. It has been desired, accordingly, that a catalyst capable of producing polymers of high melt flow rate with a lesser amount of hydrogen could be developed. In other words, a catalyst which has a high activity to hydrogen or high responsiveness to hydrogen and which gives a highly stereoregular polymer in high yield is expected to be developed. In the above-mentioned prior art, however, it is not sufficient to solve such a problem.

That is, the purpose of the present invention is to solve such a problem remaining in the prior art and to provide a solid catalyst component and catalyst for polymerization of olefins, which can afford olefin polymers in very high yield, in particular, which can afford propylene polymers in very high yield while retaining high stereoregularity, and which have a high responsiveness to hydrogen.

DISCLOSURE OF INVENTION

The present inventors worked assiduously to solve the problems remaining in the above-mentioned prior art and found that a solid catalyst component comprising a magnesium compound, titanium tetrachloride, and a particular phthalic acid diester or a derivative thereof exhibit very high activity in polymerization of olefins, particularly in polymerization of propylene to give propylene polymers in high yield with retaining a high stereoregularity, and moreover the components have high competence to hydrogen. Thus, the invention was completed.

That is, the solid catalyst component (hereinafter sometimes referred to as "component (A)") for polymerization of olefins to attain the above-mentioned purpose according to the present invention are characterized in that they comprise (a) a magnesium compound, (b) titanium tetrachloride, and (c) a phthalic acid diester or a derivative thereof of the following general formula (1):

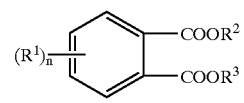

(1)

(wherein $R^1$ is an alkyl group of 1 to 8 carbon atoms or halogen atom; $R^2$ and $R^3$ are the same or different, representing an alkyl group of 1 to 12 carbon atoms; the number n of the substituent $R^1$ is 0, 1 or 2, and when n is 2, $R^1$ may be the same or different; provided that when n is 0, $R^2$ and $R^3$ each is an alkyl group of 4 to 8 carbon atoms having a tertiary carbon atom).

Moreover, the catalysts for polymerization of olefins in the present invention comprise:

(A) the above-mentioned solid catalyst components for polymerization of olefins;

(B) an organoaluminum compound of the following general formula (2):

$$R^4_p AlQ_{3-p} \tag{2}$$

(wherein $R^4$ is an alkyl group of 1 to 4 carbon atoms; Q is hydrogen atom or halogen atom; and p is an integer of $0 < p \leq 3$); and (C) an organosilicon compound of the following general formula (3):

$$R^5_q Si(OR^6)_{4-q} \tag{3}$$

(wherein $R^5$ is the same or different, representing an alkyl group of 1 to 12 carbon atoms, a cycloalkyl group, a phenyl group, a vinyl group, an allyl group, or an aralkyl group; $R^6$ is the same or different, representing an alkyl group of 1 to 4 carbon atoms, a cycloalkyl group, a phenyl group, a vinyl group, an allyl group, or an aralkyl group; q is an integer of $0 \leq q \leq 3$).

BEST MODE FOR CARRYING OUT THE INVENTION

Figure 1:
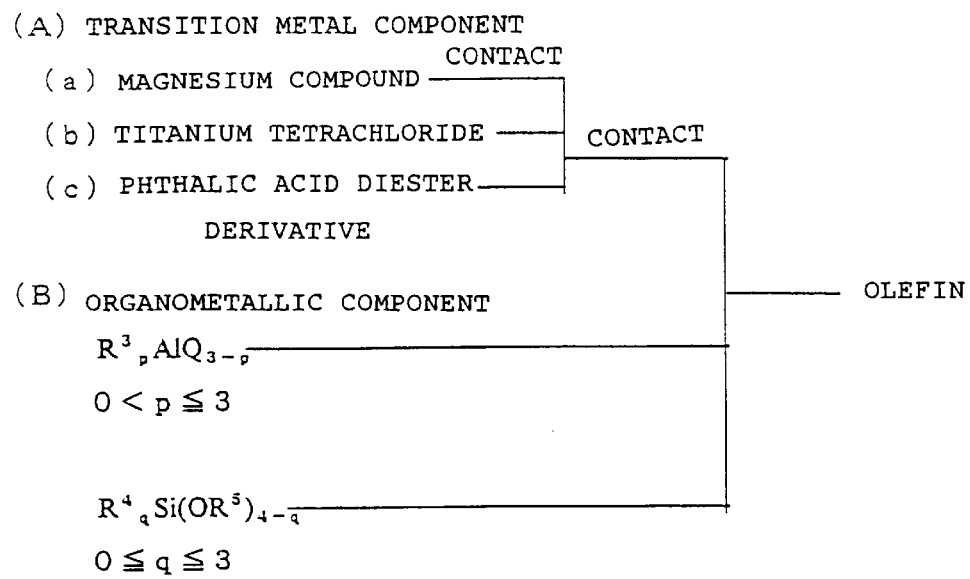
FIG. 1 is a flowchart illustrating a process for preparing the catalyst for polymerization in the present invention.

The magnesium compound used in preparation of the component (A) in the present invention (hereinafter sometimes referred to as "component (a)") include magnesium dihalide, dialkyl magnesium, alkylmagnesium halide, dialkoxymagnesium, diaryloxymagnesium, alkoxymagnesium halide, fatty acid magnesium, and the like.

Specific examples of the magnesium dihalide include magnesiumdichloride, magnesiumdibromide, magnesiumdiiodide, magnesium difluoride, and the like. The dialkylmagnesium may preferably be represented by the general formula $R^7R^8Mg$ (wherein $R^7$ and $R^8$ are the same or different, representing an alkyl group of 1 to 10 carbon atoms), more specifically including dimethylmagnesium, diethylmagnesium, methylethylmagnesium, dipropylmagnesium, methylpropylmagnesium, ethylpropyl magnesium, dibutylmagnesium, methylbutylmagnesium, ethylbutylmagnesium, and the like. The dialkylmagnesium may be prepared by reacting metal magnesium with a hydrocarbon halide or alcohol.

The alkylmagnesium halide is preferably represented by the general formula $R^9MgD_1$ (wherein $R^9$ is an alkyl group of 1 to 10 carbon atoms; and $D^1$ is a halogen atom such as chlorine atom, bromine atom, iodine atom, or fluorine atom), more specifically including ethyl-magnesium chloride, propylmagnesium chloride, butylmagnesium chloride, and the like. The magnesium halide may be prepared by reacting metal magnesium with a hydrocarbon halide or alcohol.

The dialkoxymagnesium or diaryloxymagnesium is preferably represented by the general formula $Mg(OR^{10})(OR^{11})$ (wherein $R^{10}$ and $R^{11}$ are the same or different, representing an alkyl group of 1 to 10 carbon atoms or aryl group), more specifically including dimethoxymagnesium, diethoxymagnesium, dipropoxymagnesium, dibutoxymagnesium, diphenoxymagnesium, ethoxymethoxymagnesium, ethoxypropoxy magnesium, butoxyethoxymagnesium, and the like. The dialkoxymagnesium or diaryloxymagnesium may be prepared by reacting metal magnesium with an alcohol in the presence of a halogen or halogen-containing metal compound.

The alkoxymagnesium halide is preferably represented by the general formula $Mg(OR^{12})D^2$ (wherein $R^{12}$ is an alkyl group of 1 to 10 carbon atoms; $D^2$ is a halogen atom such as chlorine atom, bromine atom, iodine atom, or fluorine atom), more specifically including methoxy-magnesium chloride, ethoxymagnesium chloride, propoxymagnesium chloride, butoxymagnesium chloride, and the like.

The fatty acid magnesium is preferably represented by the general formula $Mg(R^{13}COO)_2$ (wherein $R^{13}$ is an alkyl group of 1 to 20 carbon atoms), more specifically including magnesium laurate, magnesium stearate, magnesium octanoate, magnesium decanoate, and the like.

Among these magnesium compounds in the present invention, the dialkoxymagnesium is preferred, particularly diethoxymagnesium and dipropoxymagnesium are preferably used. The above-mentioned magnesium compounds may be used alone or in a combination of two or more.

When the dialkoxymagnesium is used as the component (a) in the invention, the alkoxymagnesium is in a form of granules or powder, which may also be used in an amorphous or spherical shape. For example, when the dialkoxymagnesium is used in a spherical shape, it is possible to obtain polymer powder which has a better granular form and narrower particle size distribution. Thus, handling and operability of the produced polymer powder during polymerization procedure are improved, and such a problem as obstruction, etc., caused by fine powder contained in the produced polymer powder can be solved.

The above-mentioned dialkoxymagnesium in a spherical shape needn't necessarily be completely round, and may be used in an ellipsoidal or pebble-like. Specifically, the ratio (l/w) of the longitudinal axis (l) to the minor axis (w) is usually 3 or less, preferably from 1 to 2, more preferably from 1 to 1.5, in the granular shape. Methods for producing such a spherical dialkoxymagnesium are described in, for example, JP-A 58-41832/1983, JP-A 62-51633/1987, JP-A 3-74341/1991, JP-A 4-368391/1992, and JP-A 8-73388/1996.

The mean particle size of the above-mentioned dialkoxymagnesium is usually from 1 to 200 μm, preferably from 5 to 150 μm. In the spherical dialkoxymagnesium, the mean particle size is usually from 1 to 100 μm, preferably from 5 to 50 μm, more preferably from 10 to 40 μm. As for particle size, it is desirable to use those in which the content of fine and coarse powder is small and the particle size distribution is limited. Specifically, the content of the granule of 5 μm or less is 20% or less, preferably 10% or less. On the other hand, that of 100 μm or more is 10% or less, preferably 5% or less. Moreover, the particle size distribution represented by ln(D90/D10)(wherein D90 means particle size at 90% of integrated particle size, and D10 means particle size at 10% of integrated particle size) is 3 or less, preferably 2 or less.

In the present invention, though titanium tetrachloride (hereinafter sometimes referred to as "component (b)") is used in preparation of the component (A), other type of titanium halides than titanium tetrachloride may also be used with titanium tetrachloride. The titanium halide is exemplified by an alkoxytitanium chloride of the general formula $Ti(OR^{14})_nCl_{4-n}$ (wherein $R^{14}$ is an alkyl group of 1 to 4 carbon atoms; and n is an integer of $1 \leq n \leq 3$). The above-mentioned titanium halide may be used alone or in a combination of two or more. Specifically, $Ti(OCH_3)Cl_3$, $Ti(OC_2H_5)Cl_3$, $Ti(OC_3H_7)Cl_3$, $Ti(O\text{-n-}C_4H_9)Cl_3$, $Ti(OCH_3)_2Cl_2$, $Ti(OC_2H_5)_2Cl_2$, $Ti(OC_3H_7)_2Cl_{2638\,6}$, $Ti(O\text{-n-}C_4H_9)_2Cl_2$, $Ti(OCH_3)_3Cl$, $Ti(OC_2H_5)_3Cl$, $Ti(OC_3H_7)_3Cl$, $Ti(O\text{-n-}C_4H_9)_3Cl$, and the like are exemplified.

As for the phthalic acid diesters or their derivatives (hereinafter sometimes referred to as "component (c)") used in preparation of the component (A) in the present invention, $R^1$ in the above-mentioned general formula (1) includes alkyl groups of 1 to 8 carbon atoms, specifically including methyl group, ethyl group, n-propyl group, isopropyl group, n-butyl group, isobutyl group, tert-butyl group, n-pentyl group, isopentyl group, neopentyl group, n-hexyl group, isohexyl group, 2,2-dimethylbutyl group, 2,2-dimethylpentyl group, isooctyl group, 2,2-dimethylhexyl group, and the like, and halogen atom such as fluorine atom, chlorine atom, bromine atom, and iodine atom; preferably, methyl group, ethyl group, tert-butyl group, chlorine atom, bromine atom or fluorine atom is exemplified, and more preferably, methyl group, tert-butyl group, chlorine atom, bromine atom or fluorine atom is exemplified.

In $R^2$ and $R^3$ of the above-mentioned general formula (1), the alkyl group of 1 to 8 carbon atoms includes the same groups as those of $R^1$ as mentioned above; and the alkyl group of 9 to 12 carbon atoms includes n-nonyl group, isononyl group, n-decyl group, isodecyl group, and n-dodecyl group. Among these groups, preferred are ethyl group, n-butyl group, isobutyl group, tert-butyl group, neopentyl group, isohexyl group, and iso-octyl group, and particularly preferred are ethyl group, n-butyl group, neopentyl group, and isohexyl group.

When the number n of the substituent $R^1$ is 1, $R^1$ is substituted for the hydrogen atom at the 3, 4 or 5 position of the phthalic acid derivative of the above general formula (1). When n is 2, $R^1$ is substituted for the hydrogen atoms at the 4 and 5 positions. However, the substituent $R^1$ is preferably substituted at least for the hydrogen atom at the 4 or 5 position of the benzene ring.

In the present invention, the phthalic acid diesters and their derivatives represented by the above-mentioned general formula (1), when n is 0 and $R^2$ and $R^3$ each is an alkyl group of 4 to 8 carbon atoms having a tertiary carbon atom, specifically include ethyl neopentyl phthalate, butyl neopenthyl phthalate, tert-butyl neopentyl phthalate, isohexyl neopentyl phthalate, dineopentyl phthalate, isooctyl neopentyl phthalate, and the like. In the above general formula (1), when n is 1 or 2, $R^1$ is an alkyl group of 1 to 5 carbon atoms or halogen atom, and $R^2$ and $R^3$ each is an alkyl group of 4 to 8 carbon atoms having a tertiary carbon atom, they include dineopentyl 3-methylphthalate, dineopentyl 4-methylphthalate, dineopentyl 3-ethylphthalate, dineopentyl 4-ethylphthalate, tert-butyl neopentyl 3-methylphthalate, tert-butyl neopentyl 4-methylphthalate, tert-butyl neopentyl 3-ethylphthalate, tert-butyl neopentyl 4-ethylphthalate, dineopentyl 4,5-dimethylphthalate, dineopentyl 4,5-diethylphthalate, tert-butyl neopentyl 4,5-dimethylphthalate, tert-butyl neopentyl 4,5-diethylphthalate, dineopentyl 3-fluorophthalate, dineopentyl 3-chlorophthalate, dineopentyl 4-chlorophthalate, dineopentyl 4-bromophthalate, and dineopentyl 4-tert-butylphthalate. Among these compounds, preferred are dineopentyl phthalate, dineopentyl 4-methylphthalate, dineopentyl 4,5-dimethylphthalate, dineopentyl 4-ethylphthalate, dineopentyl 4,5-diethyl-phthalate, dineopentyl 4-bromophthalate, dineopentyl 4-tert-butylphthalate, tert-butyl neopentyl phthalate, and dineopentyl 3-fluorophthalate.

In the above general formula, where n is 2, one of $R^1$ is a halogen atom and the other is an alkyl of 1 to 8 carbon atoms, and at least one of $R^2$ and $R^3$ is an alkyl of 1 to 12 carbon atoms other than the alkyl groups of 4 to 8 carbon atoms having a tertiary carbon atom, they include diethyl 4-methyl-5-chlorophthalate, diethyl 4-methyl-5-bromophthalate, diethyl 4-ethyl-5-chlorophthalate, diethyl 4-ethyl-5-bromophthalate di-n-butyl 4-methyl-5-chlorophthalate, di-n-butyl 4-methyl-5-bromophthalate, di-n-butyl 4-ethyl-5-chlorophthalate, di-n-butyl 4-ethyl-5-bromophthalate, diisobutyl 4-methyl-5-chloro-phthalate, diisobutyl 4-methyl-5-bromophthalate, diisobutyl 4-ethyl-5-chlorophthalate, diisobutyl 4-ethyl-5-bromo-phthalate, diisohexyl 4-methyl-5-chlorophthalate, diisohexyl 4-methyl-5-bromophthalate, diisohexyl 4-ethyl-5-chlorophthalate, diisohexyl 4-ethyl-5-bromophthalate, diisooctyl 4-methyl-5-chlorophthalate, diisooctyl 4-methyl-5-bromophthalate, diisooctyl 4-ethyl-5-chlorophthalate, diisooctyl 4-ethyl-5-bromophthalate, ethyl-n-butyl 4-methyl-5-chlorophthalate, ethyl-n-butyl 4-chloro-5-methylphthalate, ethyl-n-butyl 4-methyl-5-bromophthalate, ethyl-n-butyl 4-bromo-5-methylphthalate, ethyl-n-butyl 4-ethyl-5-chloro-phthalate, ethyl-n-butyl 4-chloro-5-ethylphthalate, ethyl-n-butyl 4-ethyl-5-bromophthalate, ethyl-n-butyl 4-bromo-5-ethyl-phthalate, ethyl isobutyl 4-methyl-5-chlorophthalate, ethyl isobutyl 4-chloro-5-methylphthalate, ethyl isobutyl 4-methyl-5-bromophthalate, ethyl isobutyl 4-bromo-5-methyl-phthalate, ethyl isobutyl 4-ethyl-5-chlorophthalate, ethyl isobutyl 4-chloro-5-ethylphthalate, ethyl isobutyl 4-ethyl-5-bromophtalate, ethyl isobutyl 4-bromo-5-ethyl-phthalate, ethyl isohexyl 4-methyl-5-chlorophthalate, ethyl isohexyl 4-chloro-5-methylphthalate, ethyl isohexyl 4-methyl-5-bromo phthalate, ethyl isohexyl 4-bromo-5-methyl-phthalate, ethyl isohexyl 4-ethyl-5-chlorophthalate, ethyl isohexyl 4-chloro-5-ethylphthalate, ethyl isohexyl 4-ethyl-5-bromo phthalate, ethyl isohexyl 4-bromo-5-ethylphthalate, n-butyl isobutyl 4-methyl-5-chlorophthalate, n-butyl isobutyl 4-chloro-5-methylphthalate, n-butyl isobutyl 4-methyl-5-bromophthalate, n-butyl isobutyl 4-bromo-5-methyl phthalate, n-butyl isobutyl 4-ethyl-5-chlorophthalate, n-butyl isobutyl 4-chloro-5-ethylphthalate, n-butyl isobutyl 4-ethyl-5-bromophthalate, n-butyl isobutyl 4-bromo-5-ethyl phthalate, n-butyl isohexyl 4-methyl-5-chlorophthalate, n-butyl isohexyl 4-chloro-5-methylphthalate, n-butyl isohexyl 4-methyl-5-bromophthalate, n-butyl isohexyl 4-bromo-5-methylphthalate, n-butyl isohexyl 4-ethyl-5-chlorophthalate, n-butyl isohexyl 4-chloro-5-ethylphthalate, n-butyl isohexyl 4-ethyl-5-bromophthalate, and n-butyl isohexyl 4-bromo-5-ethylphthalate. In the above general formula, where n is 1 or 2, $R^1$ is an alkyl group of 1 to 8 carbon atoms, and $R^2$ and $R^3$ each is an alkyl of 1 to 12 carbon atoms other than the alkyl groups of 4 to 8 carbon atoms both having a tertiary carbon atom, they include diethyl 3-methylphthalate, diethyl 4-methylphthalate, diethyl 3-ethylphthalate, diethyl 4-ethylphthalate, diethyl 3-tert-butylphthalate, diethyl 4-tert-butylphthalate, diethyl 3-n-butylphthalate, diethyl 4-n-butylphthalate, diethyl 4,5-dimethylphthalate, diethyl 4,5-diethylphthalate, diethyl 4-methyl-5-ethylphthalate, diethyl 4-methyl-5-tert-butyl-phthalate, diethyl 4-ethyl-5-tert-butylphthalate, di-n-butyl 3-methylphthalate, di-n-butyl 4-methylphthalate, di-n-butyl 3-ethylphthalate, di-n-butyl 4-ethylphthalate, di-n-butyl 3-tert-butylphthalate, di-n-butyl 4-tert-butylphthalate, di-n-butyl 3-n-butylphthalate, di-n-butyl 4-n-butylphthalate, di-n-butyl 4,5-dimethylphthalate, di-n-butyl 4,5-diethylphthalate, di-n-butyl 4-methyl-5-ethylphthalate, di-n-butyl 4-methyl-5-tert-butylphthalate, di-n-butyl 4-ethyl-5-tert-butylphthalate, diisobutyl 3-methylphthalate, diisobutyl 4-methylphthalate, diisobutyl 3-ethylphthalate, diisobutyl 4-ethylphthalate, diisobutyl 3-tert-butylphthalate, diisobutyl 4-tert-butylphthalate, diisobutyl 3-n-butylphthalate, diisobutyl 4-n-butylphthalate, diisobutyl 4,5-dimethyl-phthalate, diisobutyl 4,5-diethylphthalate, diisobutyl 4-methyl-5-ethylphthalate, diisobutyl 4-methyl-5-tert-butyl-phthalate, diisobutyl 4-ethyl-5-tert-butylphthalate, diisohexyl 3-methylphthalate, diisohexyl 4-methylphthalate, diisohexyl 3-ethylphthalate, diisohexyl 4-ethylphthalate, diisohexyl 3-tert-butylphthalate, diisohexyl 4-tert-butyl-phthalate, diisohexyl 3-n-butylphthalate, diisohexyl 4-n-butylphthalate, diisohexyl 4,5-dimethylphthalate, diisohexyl 4,5-diethylphthalate, diisohexyl 4-methyl-5-ethylphthalate, diisohexyl 4-methyl-5-tert-butylphthalate, diisohexyl 4-ethyl-5-tert-butylphthalate, diisooctyl 3-methylphthalate, diisooctyl 4-methylphthalate, diisooctyl 3-ethylphthalate, diisooctyl 4-ethylphthalate, diisooctyl 3-tert-butyl-phthalate, diisooctyl 4-tert-butylphthalate, diisooctyl 3-n-butylphthalate, diisooctyl 4-n-butylphthalate, diisooctyl 4,5-dimethylphthalate, diisooctyl 4,5-diethylphthalate, diisooctyl 4-methyl-5-ethylphthalate, diisooctyl 4-methyl-5-tert-butylphthalate, diisooctyl 4-ethyl-5-tert-butyl-phthalate, di-n-decyl 4-methylphthalate, diisodecyl 4-methylphthalate, di-n-decyl 4-ethylphthalate, diisodecyl 4-ethylphthalate, ethyl n-butyl 3-methylphthalate, ethyl n-butyl 4-methylphthalate, ethyl n-butyl 3-ethylphthalate, ethyl n-butyl 4-ethylphthalate, ethyl n-butyl 3-tert-butylphthalate, ethyl n-butyl 4-tert-butylphthalate, ethyl n-butyl 4,5- dimethylphthalate, ethyl n-butyl 4,5-diethylphthalate, ethyl n-butyl 4-methyl-5-ethylphthalate, ethyl n-butyl 4-ethyl-5-methylphthalate, ethyl isobutyl 3-methylphthalate, ethyl isobutyl 4-methylphthalate, ethyl isobutyl 3-ethylphthalate, ethyl isobutyl 4-ethylphthalate, ethyl isobutyl 3-tert-butylphthalate, ethyl isobutyl 4-tert-butylphthalate, ethyl isobutyl 4,5-dimethylphthalate, ethyl isobutyl 4,5-diethylphthalate, ethyl isobutyl 4-methyl-5-ethylphthalate, ethyl isobutyl 4-ethyl-5-methylphthalate, ethyl isohexyl 3-methylphthalate, ethyl isohexyl 4-methylphthalate, ethyl isohexyl 3-ethylphthalate, ethyl isohexyl 4-ethylphthalate, ethyl isohexyl 3-tert-butylphthalate, ethyl isohexyl 4-tert-butylphthalate, ethyl isohexyl 4,5-dimethylphthalate, ethyl isohexyl 4, 5-diethylphthalate, ethyl isohexyl 4-methyl-5-ethylphthalate, ethyl isohexyl 4-ethyl-5-methyl-phthalate, n-butyl isobutyl 3-methylphthalate, n-butyl isobutyl 4-methylphthalate, n-butyl isobutyl 3-ethylphthalate, n-butyl isobutyl 4-ethylphthalate, n-butyl isobutyl 3-tert-butylphthalate, n-butyl isobutyl 4-tert-butylphthalate, n-butyl isobutyl 4,5-dimethylphthalate, n-butyl isobutyl 4,5-diethylphthalate, n-butyl isobutyl 4-methyl-5-ethylphthalate, n-butyl isobutyl 4-ethyl-5-methylphthalate, n-butyl isohexyl 3-methylphthalate, n-butyl isohexyl 4-methylphthalate, n-butyl isohexyl 3-ethylphthalate, n-butyl isohexyl 4-ethyl-phthalate, n-butyl isohexyl 3-tert-butylphthalate, n-butyl isohexyl 4-tert-butylphthalate, n-butyl isohexyl 4,5-dimethylphthalate, n-butyl isohexyl 4,5-diethylphthalate, n-butyl isohexyl 4-methyl-5-ethylphthalate, and n-butyl isohexyl 4-ethyl-5-methylphthalate. In the above general formula (1), where n is 1 and $R^1$ is an alkyl of 1 to 5 carbon atoms or n is 2 and $R^1$ is an alkyl group of 1 to 5 carbon atoms or halogen atom, and where only one of $R^2$ and $R^3$ is an alkyl group of 4 to 8 carbon atoms having a tertiary carbon atom, the following compounds are specifically included: ethyl tert-butyl 3-methylphthalate, ethyl tert-butyl 4-methylphthalate, ethyl tert-butyl 3-ethylphthalate, ethyl tert-butyl 4-ethylphthalate, ethyl tert-butyl 4,5-dimethylphthalate, ethyl tert-butyl 4,5-diethylphthalate, ethyl tert-butyl 4-methyl-5-ethylphthalate, ethyl tert-butyl 4-ethyl-5-methylphthalate, ethyl tert-butyl 4-methyl-5-chlorophthalate, ethyl tert-butyl 4-chloro-5-methylphthalate, ethyl tert-butyl 4-methyl-5-bromophthalate, ethyl tert-butyl 4-bromo-5-methylphthalate, ethyl tert-butyl 4-ethyl-5-chlorophthalate, ethyl tert-butyl 4-chloro-5-ethylphthalate, ethyl tert-butyl 4-ethyl-5-bromophthalate, ethyl tert-butyl 4-bromo-5-ethylphthalate, ethyl neopentyl 3-methylphthalate, ethyl neopentyl 4-methylphthalate, ethyl neopentyl 3-ethylphthalate, ethyl neopentyl 4-ethylphthalate, ethyl neopentyl 4,5-dimethylphthalate, ethyl neopentyl 4,5-diethylphthalate, ethyl neopentyl 4-methyl-5-ethylphthalate, ethyl neopentyl 4-ethyl-5-methylphthalate, ethyl neopentyl 4-methyl-5-chlorophthalate, ethyl neopentyl 4-chloro-5-methylphthalate, ethyl neopentyl 4-methyl-5-bromophthalate, ethyl neopentyl 4-bromo-5-methylphthalate, ethyl neopentyl 4-ethyl-5-chlorophthalate, ethyl neopentyl 4-chloro-5-ethylphthalate, ethyl neopentyl 4-ethyl-5-bromophthalate, ethyl neopentyl 4-bromo-5-ethylphthalate, n-butyl neopentyl 3-methylphthalate, n-butyl neopentyl 4-methylphthalate, n-butyl neopentyl 3-ethylphthalate, n-butyl neopentyl 4-ethylphthalate, n-butyl neopentyl 4,5-dimethylphthalate, n-butyl neopentyl 4,5-diethylphthalate, n-butyl neopentyl 4-methyl-5-ethylphthalate, n-butyl neopentyl 4-ethyl-5-methylphthalate, n-butyl neopentyl 4-methyl-5-chlorophthalate, n-butyl neopentyl 4-chloro-5-methylphthalate, n-butyl neopentyl 4-methyl-5-bromophthalate, n-butyl neopentyl 4-bromo-5-methylphthalate, n-butyl neopentyl 4-ethyl-5-chlorophthalate, n-butyl neopentyl 4-chloro-5-ethylphthalate, n-butyl neopentyl 4-ethyl-5-bromophthalate, and n-butyl neopentyl 4-bromo-5-ethylphthalate. In the above general formula (1), where n is 1 or 2, $R^1$ is an alkyl group of 6 to 8 carbon atoms, and $R^2$ and $R^3$ each is an alkyl group of 4 to 8 carbon atoms both having a tertiary carbon atom, the following compounds are included: di-tert-butyl 4-n-hexylphthalate, di-tert-butyl 4-isohexylphthalate, di-tert-butyl 4-(2,2-dimethylbutyl)-phthalate, di-tert-butyl 4-(2,2-dimethylpentyl)phthalate, di-tert-butyl isooctylphthalate, di-tert-butyl 4-n-hexyl-5-chlorophthalate, di-tert-butyl 4-n-hexyl-5-bromophthalate, di-tert-butyl 4-isohexyl-5-chlorophthalate, di-tert-butyl 4-isohexyl-5-bromophthalate, di-tert-butyl 4-(2,2-dimethyl-butyl)-5-chlorophthalate, di-tert-butyl 4-(2,2-dimethyl-butyl)-5-bromophthalate, di-tert-butyl 4-(2,2-dimethyl-pentyl)phthalate, di-tert-butyl isooctylphthalate, dineopentyl 4-n-hexylphthalate, dineopentyl 4-isohexyl-phthalate, dineopentyl 4-(2,2-dimethylbutyl)phthalate, dineopentyl 4-(2,2-dimethylpentyl)phthalate, dineopentyl isooctylphthalate, dineopentyl 4-n-hexyl-5-chlorophthalate, dineopentyl 4-n-hexyl-5-bromophthalate, dineopentyl 4-isohexyl-5-chlorophthalate, dineopentyl 4-isohexyl-5-bromophthalate, dineopentyl 4-(2,2-dimethylbutyl)-5-chlorophthalate, dineopentyl 4-(2,2-dimethylbutyl)-5-bromophthalate, dineopentyl 4-(2,2-dimethylpentyl) phthalate, and dineopentyl isooctylphthalate.

Among these compounds, the followings are preferred: diethyl 4-methylphthalate, di-n-butyl 4-methylphthalate, diisobutyl 4-methylphthalate, diisohexyl 4-methylphthalate, diisooctyl 4-methylphthalate, diethyl 4-ethylphthalate, di-n-butyl 4-ethylphthalate, diisobutyl 4-ethylphthalate, diisohexyl 4-ethylphthalate, diisooctyl 4-ethylphthalate, diethyl 4-tert-butylphthalate, di-n-butyl 4-tert-butyl-phthalate, diisobutyl 4-tert-butylphthalate, diisohexyl 4-tert-butylphthalate, diisooctyl 4-tert-butylphthalate, diethyl 4,5-dimethylphthalate, di-n-butyl 4,5-dimethyl-phthalate, diisohexyl 4,5-dimethylphthalate, diisooctyl 4,5-dimethylphthalate, diethyl 4,5-diethylphthalate, di-n-butyl 4,5-diethylphthalate, diisohexyl 4,5-diethylphthalate, diisooctyl 4,5-diethylphthalate, diethyl 4-methyl-5-chlorophthalate, diethyl 4-methyl-5-bromophthalate, diethyl 4-ethyl-5-chlorophthalate, diethyl 4-ethyl-5-bromophthalate, di-n-butyl 4-methyl-5-chlorophthalate, di-n-butyl 4-methyl-5-bromophthalate, di-n-butyl 4-ethyl-5-chlorophthalate, di-n-butyl 4-ethyl-5-bromophthalate, diisobutyl 4-methyl-5-chlorophthalate, diisobutyl 4-methyl-5-bromophthalate, diisobutyl 4-ethyl-5-chlorophthalate, diisobutyl 4-ethyl-5-bromophthalate, diisohexyl 4-methyl-5-chlorophthalate, diisohexyl 4-methyl-5-bromophthalate, diisohexyl 4-ethyl-5-chlorophthalate, diisohexyl 4-ethyl-5-bromophthalate, diisooctyl 4-methyl-5-chlorophthalate, diisooctyl 4-methyl-5-bromophthalate, diisooctyl 4-ethyl-5-chlorophthalate, and diisooctyl 4-ethyl-5-bromophthalate.

When n is 1 or 2, $R^1$ is a halogen atom, and at least one of $R^2$ and $R^3$ is not alkyl group of 4 to 8 carbon atoms having a tertiary carbon atom, the following compounds are included: diethyl 3-fluorophthalate, diethyl 4-fluorophthalate, diethyl 3-chlorophthalate, diethyl 4-chlorophthalate, diethyl 3-bromophthalate, diethyl 4-bromophthalate, diethyl 3-iodo-phthalate, diethyl 4-iodophthalate, diethyl 4,5-dichloro-phthalate, diethyl 4,5-dibromophthalate, diethyl 4-chloro-5-bromophthalate, di-n-butyl 3-fluorophthalate, di-n-butyl 4-fluorophthalate, di-n-butyl 3-chlorophthalate, di-n-butyl 4-chlorophthalate, di-n- butyl 3-bromophthalate, di-n-butyl 4-bromophthalate, di-n-butyl 3-iodophthalate, di-n-butyl 4-iodophthalate, di-n-butyl 4,5-dichlorophthalate, di-n-butyl 4,5-dibromophthalate, di-n-butyl 4-chloro-5-bromophthalate, diisobutyl 3-fluorophthalate, diisobutyl 4-fluorophthalate, diisobutyl 3-chlorophthalate, diisobutyl 4-chlorophthalate, diisobutyl 3-bromophthalate, diisobutyl 4-bromophthalate, diisobutyl 3-iodophthalate, diisobutyl 4-iodophthalate, diisobutyl 4,5-dichlorophthalate, diisobutyl 4,5-dibromophthalate, diisobutyl 4-chloro-5-bromophthalate, diisohexyl 3-fluorophthalate, diisohexyl 4-fluorophthalate, diisohexyl 3-chlorophthalate, diisohexyl 4-chlorophthalate, diisohexyl 3-bromophthalate, diisohexyl 4-bromophthalate, diisohexyl 3-iodophthalate, diisohexyl 4-iodophthalate, isohexyl 4,5-dichlorophthalate, diisohexyl 4,5-dibromophthalate, diisohexyl 4-chloro-5-bromophthalate, diisooctyl 3-fluorophthalate, diisooctyl 4-fluorophthalate, diisooctyl 3-chlorophthalate, diisooctyl 4-chlorophthalate, diisooctyl 3-bromophthalate, diisooctyl 4-bromophthalate, diisooctyl 3-iodophthalate, diisooctyl 4-iodophthalate, diisooctyl 4,5-dichlorophthalate, diisooctyl 4,5-dibromophthalate, diisooctyl 4-chloro-5-bromophthalate, di-n-decyl 4-chlorophthalate, isodecyl 4-chlorophthalate, di-n-decyl 4-bromophthalate, isodecyl 4-bromophthalate, ethyl n-butyl 3-fluorophthalate, ethyl n-butyl 4-fluorophthalate, ethyl n-butyl 3-chlorophthalate, ethyl n-butyl 4-chlorophthalate, ethyl n-butyl 3-bromophthalate, ethyl n-butyl 4-bromophthalate, ethyl n-butyl 3-iodophthalate, ethyl n-butyl 4-iodophthalate, ethyl n-butyl 4,5-dichlorophthalate, ethyl n-butyl 4,5-dibromophthalate, ethyl n-butyl 4-chloro-5-bromophthalate, ethyl isobutyl 3-fluorophthalate, ethyl isobutyl 4-fluorophthalate, ethyl isobutyl 3-chlorophthalate, ethyl isobutyl 4-chlorophthalate, ethyl isobutyl 3-bromophthalate, ethyl isobutyl 4-bromophthalate, ethyl isobutyl 3-iodophthalate, ethyl isobutyl 4-iodophthalate, ethyl isobutyl 4,5-dichlorophthalate, ethyl isobutyl 4,5-dibromophthalate, ethyl isobutyl 4-chloro-5-bromophthalate, ethyl isohexyl 3-fluorophthalate, ethyl isohexyl 4-fluorophthalate, ethyl isohexyl 3-chlorophthalate, ethyl isohexyl 4-chlorophthalate, ethyl isohexyl 3-bromophthalate, ethyl isohexyl 4-bromophthalate, ethyl isohexyl 3-iodophthalate, ethyl isohexyl 4-iodophthalate, ethyl isohexyl 4,5-dichlorophthalate, ethyl isohexyl 4,5-dibromophthalate, ethyl isohexyl 4-chloro-5-bromophthalate, ethyl isobutyl 3-fluorophthalate, ethyl isobutyl 4-fluorophthalate, ethyl isobutyl 3-chlorophthalate, ethyl isobutyl 4-chlorophthalate, ethyl isobutyl 3-bromophthalate, ethyl isobutyl 4-bromophthalate, ethyl isobutyl 3-iodophthalate, ethyl isobutyl 4-iodophthalate, ethyl isobutyl 4,5-dichlorophthalate, ethyl isobutyl 4,5-dibromophthalate, ethyl isobutyl 4-chloro-5-bromophthalate, n-butyl isobutyl 3-fluorophthalate, n-butyl isobutyl 4-fluorophthalate, n-butyl isobutyl 3-chlorophthalate, n-butyl isobutyl 4-chlorophthalate, n-butyl isobutyl 3-bromophthalate, n-butyl isobutyl 4-bromophthalate, n-butyl isobutyl 3-iodophthalate, n-butyl isobutyl 4-iodophthalate, n-butyl isobutyl 4,5-dichlorophthalate, n-butyl isobutyl 4,5-dibromophthalate, n-butyl isobutyl 4-chloro-5-bromophthalate, n-butyl isohexyl 3-fluorophthalate, n-butyl isohexyl 4-fluorophthalate, n-butyl isohexyl 3-chlorophthalate, n-butyl isohexyl 4-chlorophthalate, n-butyl isohexyl 3-bromophthalate, n-butyl isohexyl 4-bromophthalate, n-butyl isohexyl 3-iodophthalate, n-butyl isohexyl 4-iodophthalate, n-butyl isohexyl 4,5-dichlorophthalate, n-butyl isohexyl 4,5-dibromophthalate, n-butyl isohexyl 4-chloro-5-bromo-phthalate, ethyl tert-butyl 3-fluorophthalate, ethyl tert-butyl 4-fluorophthalate, ethyl tert-butyl 3-chlorophthalate, ethyl tert-butyl 4-chlorophthalate, ethyl tert-butyl 3-bromo-phthalate, ethyl tert-butyl 4-bromophthalate, ethyl tert-butyl 3-iodophthalate, ethyl tert-butyl 4-iodophthalate, ethyl tert-butyl 4,5-dichlorophthalate, ethyl tert-butyl 4,5-dibromophthalate, ethyl tert-butyl 4-chloro-5-bromophthalate, ethyl neopentyl 3-fluorophthalate, ethyl neopentyl 4-fluorophthalate, ethyl neopentyl 3-chlorophthalate, ethyl neopentyl 4-chlorophthalate, ethyl neopentyl 3-bromophthalate, ethyl neopentyl 4-bromophthalate, ethyl neopentyl 3-iodo-phthalate, ethyl neopentyl 4-iodophthalate, ethyl neopentyl 4,5-dichlorophthalate, ethyl neopentyl 4,5-dibromophthalate, ethyl neopentyl 4-chloro-5-bromophthalate, n-butyl tert-butyl 3-fluorophthalate, n-butyl tert-butyl 4-fluorophthalate, n-butyl tert-butyl 3-chlorophthalate, n-butyl tert-butyl 4-chlorophthalate, n-butyl tert-butyl 3-bromophthalate, n-butyl tert-butyl 4-bromophthalate, n-butyl tert-butyl 3-iodo-phthalate, n-butyl tert-butyl 4-iodophthalate, n-butyl tert-butyl 4,5-dichlorophthalate, n-butyl tert-butyl 4,5-dibromophthalate, n-butyl tert-butyl 4-chloro-5-bromophthalate, n-butyl neopentyl 3-fluorophthalate, n-butyl neopentyl 4-fluorophthalate, n-butyl neopentyl 3-chlorophthalate, n-butyl neopentyl 4-chlorophthalate, n-butyl neopentyl 3-bromo-phthalate, n-butyl neopentyl 4-bromophthalate, n-butyl neopentyl 3-iodophthalate, n-butyl neopentyl 4-iodophthalate, n-butyl neopentyl 4,5-dichlorophthalate, n-butyl neopentyl 4,5-dibromophthalate, and n-butyl neopentyl 4-chloro-5-bromophthalate.

Among these compounds, preferred are diethyl 4-bromophthalate, di-n-butyl 4-bromophthalate, diisobutyl 4-bromophthalate, diethyl 4-chlorophthalate, di-n-butyl 4-chlorophthalate, diisobutyl 4-chlorophthalate, diisohexyl 4-chlorophthalate, diisooctyl 4-chlorophthalate, diisohexyl 4-bromophthalate, diisooctyl 4-bromophthalate, diethyl 4,5-dichlorophthalate, di-n-butyl 4,5-dichlorophthalate, diisohexyl 4,5-dichlorophthalate, and diisooctyl 4,5-dichlorophthalate.

Among the above specifically described phthalic acid diesters and derivatives thereof, the particularly preferred compound as an electron donor, one component of the catalyst for olefin polymerization, includes dineopentyl 4-methylphthalate, dineopentyl phthalate, dineopentyl 3-fluorophthalate, dineopentyl 4,5-dimethylphthalate, dineopentyl 4-bromophthalate, tert-butyl neopentyl phthalate, di-n-butyl 4-methylphthalate, di-n-butyl 4-tert-butylphthalate, diethyl 4-methylphthalate, diethyl 4-tert-butylphthalate, di-n-butyl 4-bromophthalate, di-n-butyl 4-chlorophthalate, di-n-butyl 4,5-dichlorophthalate, diisohexyl 4-bromophthalate, and dineopentyl 4-tert-butylphthalate. These phthalic acid diesters and derivatives thereof may be used alone or in a combination of two or more.

In the present invention, in addition to the phthalic acid diesters or derivatives thereof as the above component (c), another electron donor compound may be used in preparation of the component (A). Such an electron donor compound, which is an organic compound having oxygen and/or nitrogen, includes, for examples, alcohols, phenols, ethers, esters, ketones, acid halides, aldehydes, amines, amides, nitriles, isocyanates, organosilicon compounds containing a Si—O—C linkage, and the like.

Specifically, these compounds include alcohols such as methanol, ethanol, n-propanol, 2-ethylhexanol, etc., phenols such as phenol, cresol, catechol, etc., ethers such as methyl ether, ethyl ether, propyl ether, butyl ether, amyl ether, diphenyl ether, etc., monocarboxylic acid esters such as methyl formate, ethyl acetate, vinyl acetate, propyl acetate, octyl acetate, cyclohexyl acetate, ethyl propionate, ethyl butyrate, methyl benzoate, ethyl benzoate, propyl benzoate, butyl benzoate, octyl benzoate, cyclohexyl benzoate, phenyl benzoate, methyl p-toluate, ethyl p-toluate, methyl anisate, ethyl anisate, etc., dicarboxylic acid esters such as diethylmaleate, dibutyl maleate, dioctyl maleate, dimethyl adipate, diethyl adipate, dipropyl adipate, dibutyl adipate, diisodecyl adipate, dioctyl adipate, dimethyl phthalate, diethyl phthalate, di-n-propyl phthalate, di-n-butyl phthalate, di-isobutyl phthalate, di-n-pentyl phthalate, di-n-hexyl phthalate, di-n-heptyl phthalate, di-n-octyl phthalate, di-isooctyl phthalate, di-n-nonyl phthalate, di-n-decyl phthalate, etc., ketones such as acetone, methyl ethyl ketone, methyl butyl ketone, acetophenone, benzophenone, etc., acid halides such as phthalic acid dichloride, terephthalic acid dichloride, etc., aldehydes such as acetaldehyde, propionaldehyde, octylaldehyde, benz-aldehyde, etc., amines such as methylamine, ethylamine, tributylamine, piperidine, aniline, pyridine, etc., amides such as oleic acid amide, stearic acid amide, etc., nitriles such as acetonitrile, benzonitrile, tolunitrile, etc., isocyanates such as methyl isocyanate, ethyl isocyanate, etc.

The organosilicon compound containing a Si—O—C linkage includes phenylalkoxysilanes, alkylalkoxysilanes, phenylalkylalkoxysilanes, cycloalkylalkoxysilane, cycloalkylalkyl alkoxysilane, and the like.

Among the above electron donor compounds, the esters, particularly phthalic acid diesters, maleic acid diesters and phenols other than the component (c), are preferred.

In preparation of the component (A) in the present invention, in addition to the above-mentioned essential component, an aluminum compound such as aluminum trichloride, diethoxy-aluminum chloride, diisopropoxyaluminum chloride, ethoxy-aluminum dichloride, isopropoxyaluminum dichloride, butoxy-aluminum dichloride and (or) triethoxyaluminum, or an organic acid metal salt such as sodium stearate, magnesium stearate, aluminum stearate, or a polysiloxane such as chain or partially hydrogenated or cyclic or denatured polysiloxane which is liquid or viscous at ordinary temperature, may be used.

The above-mentioned component (A) may be prepared, as mentioned above, by making the component (a), component (b) and component (c) contact with each other. The contact is preferably carried out in the presence of an inert organic solvent in view of easiness of operation, though it may be processed in the absence of the solvent. The inert organic solvent used includes saturated hydrocarbon compounds such as hexane, heptane and (or) cyclohexane, aromatic hydrocarbon compounds such as benzene, toluene, xylene and (or) ethylbenzene, and halogenated hydrocarbon compounds such as o-dichloro-benzene, methylene chloride, carbon tetrachloride and (or) dichloroethane. Among these compounds, an aromatic hydrocarbon compound which is in a liquid state at ordinary temperature and has the boiling point at approximately 90 to 150° C., may preferably be used, specifically including toluene, xylene, ethylbenzene, etc.

As for methods for preparing the component (A), the followings are exemplified: a method in which a magnesium compound in the above component (a) is dissolved in an alcohol or titanium compound and made contact or heated with the component (b) or the components (b) and (c) to yield a solid component as precipitate; and a method in which the component (a) is suspended in the component (b) or an inert hydrocarbon solvent, which is then made contact with the component (c) or the components (c) and (b) to yield the component (A).

Among these methods, the particle of solid catalyst component obtained in the former is nearly spherical and its size distribution is sharp. In the latter method, where a spherical magnesium compound is used, a solid catalyst component of which the particle is spherical and has sharp size distribution can be obtained. Moreover, even when no spherical magnesium compound is used, similarly, a solid catalyst component of which the particle is spherical and has sharp size distribution can be obtained by forming the particles by a spray-drying process, for example, spray drying of a solution or suspension using a sprayer.

The contact of each component may be carried out in a moisture-free condition under an inert gas atmosphere with stirring in a vessel equipped with a stirrer. The contact temperature, when it is carried out with simple stirring or under dispersing or suspending for denaturation processing, may be in a range of relatively low temperature around room temperature. When the product is obtained by reaction after contact, however, the temperature is preferably kept in a range of 40 to 130° C. At a temperature lower than 40° C., the reaction does not proceed well, and consequently produces a solid catalyst component insufficient in performance. At a temperature over 130° C., it becomes difficult to control the reaction because of markedly increased vaporization of the solvent used. The reaction is conducted for a period of 1 minute or longer, preferably 10 minutes or longer, more preferably 30 minutes or longer.

The method for preparing the component (A) is illustrated as follows.

(1) A method comprises: a solution of magnesium chloride dissolved in a tetra-alkoxytitanium is brought into contact with polysiloxane to yield a solid product, which is then allowed to cataliytcally react with titanium tetrachloride and then with the component (c) to yield the component (A). In this reaction, the component (A) may preliminarily be treated with an organoaluminum compound, an organosilicon compound and an olefin for polymerization.

(2) A method in which anhydrous magnesium chloride is allowed to react with 2-ethylhexyl alcohol to give a, homogeneous solution, which is brought into contact with phthalic anhydride. The resulting solution is then allowed to catalytically react with titanium tetrachloride and the component (c) to yield a solid product, which is further brought into contact with titanium tetrachloride to yield the component (A).

(3) A method in which metal magnesium, butyl chloride and dibutyl ether is allowed to react to yield an organomagnesium compound, which is allowed to catalytically react with tetrabutoxytitanium and tetraethoxytitanium to give a solid product. The latter is allowed to catalytically react with the component (c), dibutyl ether and titanium tetrachloride to yield the component (A). In this reaction, the component (A) may also be prepared by preliminarily treating the solid component with an organoaluminum compound, an organosilicon compound and an olefin for polymerization.

(4) A method in which an organomagnesium compound such as dibutylmagnesium and an organoaluminum compound are allowed to catalytically react with an alcohol such as butanol and (or) 2-ethylhexyl alcohol, in the presence of a hydrocarbon solvent to give a homogeneous solution. The latter is brought into contact with a silicon compound such as $SiCl_4$, $HSiCl_3$ and/or polysiloxane, to yield a solid product. This is then allowed to catalytically react with titanium tetrachloride and the component (c) in the presence of an aromatic hydrocarbon solvent and then brought into contact with titanium tetrachloride to yield the component (A).

(5) A method in which magnesium chloride, a tetraalkoxytitanium and an aliphatic alcohol are allowed to catalytically react in the presence of an aliphatic hydrocarbon compound to give a homogeneous solution, to which is then added titanium tetrachloride. The mixture is then heated to yield a solid product, which is then allowed to contact with the component (c) and then with titanium tetrachloride to yield the component (A).

(6) A method in which metal magnesium powder, an alkyl monohalide compound and iodine are subjected to catalytic reaction. The reaction mixture is then allowed to catalytically react with a tetraalkoxytitanium, an acid halide and an aliphatic alcohol in the presence of an aliphatic hydrocarbon to give a homogeneous solution, to which is then added titanium tetrachloride. The mixture is then heated to yield a solid product, which is then allowed to contact with the component (c) and then with titanium tetrachloride to yield the component (A).

(7) A method in which diethoxymagnesium is suspended in an alkylbenzene or halogenated hydrocarbon solvent, then brought into contact with titanium tetrachloride, and then with the component (c) under heating to yield a solid product. This is washed with an alkylbenzene and then again brought into contact with titanium tetrachloride in the presence of an alkylbenzene to yield the component (A). In this reaction, the component (A) may be prepared by thermal treatment of the solid product in the presence or absence of a hydrocarbon solvent.

(8) A method in which diethoxymagnesium is suspended in an alkylbenzene and then allowed to catalytically react with titanium tetrachloride and the component (c) to yield a solid product. This is washed with an alkylbenzene and then again brought into contact with titanium tetrachloride in the presence of an alkylbenzene to yield the component (A). In this reaction, the component (A) may be prepared by contact of the solid component with titanium tetrachloride 2 times or more.

(9) A method in which diethoxy magnesium, calcium chloride and a silicon compound of the formula $Si(OR^{15})_4$ (wherein $R^{15}$ is an alkyl group or aryl group) are pulverized together, and the resulting powder is suspended in an aromatic hydrocarbon. The mixture is allowed to catatlytically react with titanium tetrachloride and the component (c) and then further brought into contact with titanium tetrachloride to yield the component (A).

(10) A method in which diethoxy magnesium and the component (c) are suspended in an alkylbenzene, which is then added to titanium tetachloride to react to yield a solid product. This is washed with an alkylbenzene and then again brought into contact with titanium tetrachloride in the presence of an alkylbenzene to yield the component (A).

(11) A method in which a calcium halide and a fatty acid magnesium such as magnesium stearate are allowed to catalytically react with titanium tetrachloride and the component (c), and then brought into contact with titanium tetrachloride to yield the component (A).

(12) A method in which diethoxymagnesium is suspended in an alkylbenzene or halogenated hydrocarbon solvent, then brought into contact with titanium tetrachloride, and then with the component (c) under heating to yield a solid product. This is washed with an alkylbenzene and then again brought into contact with titanium tetrachloride in the presence of an alkylbenzene to yield the component (A), wherein the reaction mixture is brought into contact with aluminum chloride in any step of the above suspending or contact or catalytic reaction.

(13) A method in which diethoxymagnesium, 2-ethylhexyl alcohol and carbon dioxide are subjected to catalytic reaction to give a homogeneous solution in the presence of toluene, with which titanium tetra-chloride and the component (c) are allowed to catalytically react to yield a solid product. This is dissolved in tetrahydrofuran to yield a solid product as precipitate, which is allowed to catalytically react with titanium tetrachloride, if required repeatedly, to yield the component (A). In this reaction, a silicon compound such as tetrabutoxysilane, may be used in any step of the above-mentioned contact, catalytic reaction and dissolution.

(14) A method in which magnesium chloride, an organic epoxy compound and a phosphoric acid compound are suspended into a hydrocarbon solvent such as toluene and heated to give a homogeneous solution, which is allowed to catalytically react with phthalic anhydride and titanium tetrachloride to yield a solid product. This is allowed to catalytically react with the component (c), and the resulting product is washed with analkylbenzene and then again brought into contact with titanium tetrachloride in the presence of an alkylbenzene to yield the component (A).

(15) In this method, a dialkoxymagnesium, a titanium compound and the component (c) are subjected to catalytic reaction in the presence of toluene. The resulting reaction product is allowed to catalytically react with a silicon compound such as polysiloxane, then with titanium tetrachloride, then with a metal salt of organic acid, and then again with titanium tetrachloride to yield the component (A).

In a preferred method for preparing the component (A) used in the present invention, a dialkoxymagnesium is suspended in an aromatic hydrocarbon solvent which is liquid at ordinary temperature, and then brought into contact with the component (c) and then with titanium tetrachloride to yield the component (A). Alternatively, a dialkoxymagnesium is suspended in an aromatic hydrocarbon solvent which is liquid at ordinary temperature, and then brought into contact with titanium tetrachloride and then with the component (c) to yield the component (A).

The particularly preferred method for preparing the component (A) used in the present invention is as follows. For example, a dialkoxymagnesium is suspended in an aromatic hydrocarbon solvent, which is liquid at ordinary temperature, to give a suspension, which is brought into contact with titanium tetrachloride at −20 to 100° C., preferably −10 to 70° C., more preferably 0 to 30° C., and then allowed to react at 40 to 130° C., more preferably 70 to 120° C. During this operation, before or after contact with a titanium halide, the above suspension is brought into contact with the component (c) at −20 to 130° C. to yield a solid reaction product. This is washed with an aromatic hydrocarbon compound, which is liquid at ordinary temperature, and then again allowed to catalytically react with titanium tetrachloride in the presence of an aromatic hydrocarbon compound at 40 to 130° C., more preferably at 70 to 120° C. The product is further washed with a hydrocarbon compound which is liquid at ordinary temperature to yield the component (A).

The amount of each compound to be used, though it could not be defined because it depends on the preparation method employed, for example, that of the component (b) is 0.5 to 100 mole, preferably 0.5 to 50 mole, more preferably 1 to 10 mole, for 1 mole of the component (a). The amount of the component (c) is 0.01 to 10 mole, preferably 0.01 to 1 mole, more preferably 0.02 to 0.6 mole.

The component (A) prepared as mentioned above contains magnesium, titanium, the component (c) and a halogen atom. The content of each component is but not limited to 10 to 30% by weight of magnesium, 1 to 5% by weight of titanium, 1 to 20% by weight of the component (c), and 40 to 70% by weight of halogen atom.

The organoaluminum compound (B)(hereinafter sometimes referred to as "component (B)") used in formation of the catalyst for propylene polymerization in the present invention includes those represented by the general formula $R^4{}_pAlQ_{3-p}$ (wherein $R^4$ is an alkyl group of 1 to 4 carbon atoms; Q is hydrogen atom or halogen atom; and p is an integer of $0<p\leq3$). Specific example of such an organoaluminum compound (B) includes triethyl aluminum, diethylaluminum chloride, tri-isobutylaluminum, diethylaluminum bromide, and diethylaluminum hydride, and these may be used alone or in a combination of two or more. Preferred is triethylaluminum and tri-isobutylaluminum.

The organosilicon compound (C)(hereinafter sometimes referred to as "component (C)") used in formation of the catalyst for propylene polymerization in the invention includes those represented by the general formula $R^5{}_qSi(OR^6)_{4-q}$ (wherein $R^5$ is the same or different, representing an alkyl group of 1 to 12 carbon atoms, cycloalkyl group, a phenyl group, a vinyl group, an allyl group, or an aralkyl group; $R^6$ is the same or different, representing an alkyl group of 1 to 4 carbon atoms, a cycloalkyl group, a phenyl group, a vinyl group, an allyl group, or an aralkyl group; q is an integer of $0\leq q\leq3$). Such organosilicon compounds include phenyl-alkoxysilanes, alkylalkoxysilanes, phenylalkylalkoxysilanes, cycloalkylalkoxysilanes, cycloalkylalkylalkoxysilanes, and the like.

Specific examples of the above-mentioned organosilicon compounds include: trimethylmethoxysilane, trimethylethoxysilane, tri-n-propylmethoxysilane, tri-n-propylethoxysilane, tri-n-butylmethoxysilane, tri-isobutylmethoxysilane, tri-tert-butylmethoxysilane, tri-n-butylethoxysilane, tricyclohexylmethoxysilane, tricyclohexylethoxysilane, cyclohexyldimethylmethoxysilane, cyclohexyl-diethylmethoxysilane, cyclohexyldiethylethoxysilane, di-methyldimehoxysilane, dimethyldiethoxysilane, di-n-propyl-dimethoxysilane, di-isopropyldimethoxysilane, di-n-propyl-diethoxysilane, di-isopropyldiethoxysilane, di-n-butyl-dimethoxysilane, di-isobutyldimethoxysilane, di-tert-butyl-dimethoxysilane, di-n-butyldiethoxysilane, n-butylmethyl-dimethoxysilane, bis(2-ethylhexyl) dimethoxysilane, bis(2-ethylhexyl)diethoxysilane, dicyclopentyldimethoxysilane, dicyclopentyldiethoxysilane, dicyclohexyldimethoxysilane, dicyclohexyldiethoxysilane, bis(3-methylcyclohexyl)dimethoxysilane, bis(4-methylcyclohexyl)dimethoxysilane, bis-(3,5-dimethylcyclohexyl)dimethoxysilane, cyclohexylcyclopentyl-dimethoxysilane, cyclohexylcyclopentyldiethoxysilane, cyclohexylcyclopentyldipropoxysilane, 3-methylcyclohexyl-cyclopentyldimethoxysilane, 4-methylcyclohexylcyclopentyl-dimethoxysilane, 3,5-dimethylcyclohexylcyclopentyldimethoxy-silane, 3-methylcyclohexylcyclohexyldimethoxysilane, 4-methylcyclohexylcyclohexyldimethoxysilane, 3,5-dimethyl-cyclohexylcyclohexyldimethoxysilane, cyclopentylmethyl-dimethoxysilane, cyclopentylmethyldiethoxysilane, cyclo-pentylethyldiethoxy silane, cyclopentyl(iso-propyl) dimethoxy-silane, cyclopentyl(iso-butyl)dimethoxysilane, cyclohexyl-methyldimethoxysilane, cyclohexylmethyldiethoxysilane, cyclohexylethyldimethoxysilane, cyclohexylethyldiethoxy-silane, cyclohexyl(n-propyl)dimethoxysilane, cyclohexyl-(iso-propyl)dimethoxysilane, cyclohexyl(n-propyl) diethoxy-silane, cyclohexyl(iso-butyl)dimethoxysilane, cyclohexyl(n-butyl)diethoxysilane, cyclohexyl(n-pentyl) dimethoxysilane, cyclohexyl(n-pentyl)diethoxysilane, diphenyldimethoxysilane, diphenyldiethoxysilane, phenylmethyldimethoxysilane, phenylmethyldiethoxysilane, phenylethyldimethoxysilane, phenylethyldiethoxysilane, methyltrimethoxysilane, methyl-triethoxysilane, ethyltrimethoxysilane, ethyltriethoxysilane, n-propyltrimethoxysilane, iso-propyltrimethoxysilane, n-propyltriethoxysilane, iso-propyltriethoxysilane, n-butyl-trimethoxysilane, iso-butyltrimethoxysilane, tert-butyltri-methoxysilane, n-butyltriethoxysilane, 2-ethylhexyltri-methoxysilane, 2-ethylhexyltriethoxysilane, cyclopentyl-trimethoxysilane, cyclopentyltriethoxysilane, cyclohexyl-trimethoxysilane, cyclohexyltriethoxysilane, vinyltrimethoxysilane, vinyltriethoxysilane, phenyltrimethoxysilane, phenyltriethoxysilane, tetramethoxysilane, tetraethoxysilane, tetrapropoxysilane, tetrabutoxysilane, and the like. Among the above compounds, preferably used are di-n-propyldimethoxy-silane, di-iso-propyldimethoxysilane, di-n-butyldimethoxy-silane, di-iso-butyldimethoxysilane, di-tert-butyldimethoxy-silane, di-n-butyldiethoxysilane, tert-butyltrimethoxysilane, dicyclohexyldimethoxysilane, dicyclohexyldiethoxysilane, cyclohexylmethyldimethoxysilane, cyclohexylmethyldiethoxy-silane, cyclohexylethyldimethoxysilane, cyclohexylethyldi-ethoxysilane, dicyclopentyl dimethoxysilane, dicyclopentyl-diethoxysilane, cyclopentylmethyldimethoxysilane, cyclo-pentylmethyldiethoxysilane, cyclopentylethyldiethoxysilane, cyclohexylcyclopentyldimethoxysilane, cyclohexylcyclo-pentyldiethoxysilane, 3-methylcyclohexylcyclopentyldi-methoxysilane, 4-methylcyclohexylcyclopentyldimethoxysilane, and 3,5-dimethylcyclohexylcyclopentyldimethoxysilane. The organosilicon compound (C) may be used alone or in a combination of two or more.

Next, the catalyst for polymerization of olefins of the present invention, which are composed of the above-mentioned component (A), component (B) and component (C), are applied to polymerization or co-polymerization of olefins. The olefins include ethylene, propylene, 1-butene, 1-pentene, 4-methyl-1-pentene, vinylcyclohexane, and the like, which may be used alone or in combination of two or more. Particularly, ethylene, propylene and 1-butene are preferably used. Particularly preferred is propylene. In polymerization of propylene, co-polymerization with another olefin may be achieved. The olefins used in co-polymerization include ethylene, 1-butene, 1-pentene, 4-methyl-1-pentene, vinylcyclohexane, etc., and these olefins may be used alone or in combination of two or more. Particularly ethylene and 1-butene are preferably used.

The ratio of the amount of each component to be used may optionally be determined as far as it does not effect on the result of the present invention. Though there is no particular limitation, the component (B) may be used in a range of 1 to 2000 mole, preferably 50 to 1000 mole, for 1 mole of the component (A). The component (C) may be used in a range of 0.002 to 10 mole, preferably 0.01 to 2 mole, particularly 0.01 to 0.5 mole, for 1 mole of the component (B).

Though each component may be brought into contact in optional order, it is desirous that first the organoaluminum compound (B) is placed in a polymerization medium, which is then brought into contact with the organosilicon compound (C) and then with the solid catalyst component (A).

The polymerization reaction of the present invention may be carried out in the presence or absence of an organic solvent. The olefin monomer such as propylene, may be used in a state of either gas or liquid. The polymerization is made at a temperature of 200° C. or lower, preferably 100° C. or lower at a pressure of 10 MPa or lower, preferably 5 MPa or lower. Any method of polymerization such as continuous polymerization and batch type polymerization may be employed. The polymerization reaction may be conducted in one-step or two or more steps.

Moreover, in polymerizing an olefin using a catalyst comprising the component (A), component (B) and component (C) (also referred to as main polymerization), it is desirous to make preliminary polymerization prior to main polymerization in order to improve much more catalyst activity, stereoregularity and granular properties of the polymer generated. In the preliminary polymerization, a monomer such as olefins or styrene may be used in the same manner as in the main polymerization.

In carrying out the preliminary polymerization, though each component and monomer may be brought into contact in optional order, it is preferable that first the component (B) is placed in a reaction medium for preliminary polymerization under inert gas atmosphere or such a gas as propylene used in polymerization, and brought into contact with the component (A), and then with an olefin such as propylene and/or one or two or more of other olefins. When the preliminary polymerization is carried out in combination with the component (C), it is desirous that first the component (B) is placed in a reaction medium for preliminary polymerization under inert gas atmosphere or such a gas as propylene used in polymerization, and brought into contact with the component (C), and then with the solid catalyst component (A), followed by contact with an olefin such as propylene and/or one or two or more of other olefins.

When an olefin is polymerized in the presence of a catalyst for polymerization of olefins formed in the present invention, it is possible to produce an olefin polymer in a much higher yield, while high stereoregularity being retained, than with the catalyst used in the prior art. High responsiveness to hydrogen can also be realized.

WORKING EXAMPLES

The present invention will be illustrated specifically by the following Examples, compared with Comparative Examples.

Preparation 1

In a 2.0 liter three-necked flask equipped with a refluxing condenser was introduced 25.0 g of 4-methylphthalic acid and 100.0 g of neopentyl alcohol, to which was slowly added 18 ml of sulfuric acid at 66° C., and the mixture was refluxed at a temperature of 115 to 125° C. for 2 hours. After cooling, the reaction mixture was moved into a separating funnel containing 150 ml of distilled water. The flask was washed with 200 ml of diethyl ether, and the ether was poured into the separating funnel. After flashing operation, removal of the aqueous layer (lower layer) was repeated 3 times. Then, 150 ml of 5% sodium hydrogen carbonate aqueous solution was added, and after flashing operation made, the aqueous layer showed pH 7 to 8. After removal of the aqueous layer, the organic layer was washed with 300 ml of saturated brine and then with 150 ml of distilled water. After removal of the aqueous layer, the ether layer (upper layer) was placed in an Erlenmeyer flask and dried on anhydrous sodium sulfate. Ether was distilled off under reduced pressure, and the residue was further distilled under reduced pressure. When temperature at the column top reached approximately 190° C., 13.0 g of yellow viscous liquid was obtained. This was cooled to about −10° C. to give white crystals, which were recrystallized from ethanol to give 11.8 g (26.5% yield) of white crystals in good purity. This white crystalline material was analyzed by means of MS, $^1$H-NMR and Raman spectra in respective analyzers as described below and identified to be dineopentyl 4-methyl-phthalate. The analytical values are shown in Tables 1 to 3.

Analyzers

MS was measured in an apparatus Finigan Mat (GC-MS), and $^1$H-NMR was measured in an apparatus JEOL GSX270, where $CDCl_3$ was used as solvent. Raman spectra were measured in an apparatus JEOL RFT800.

Preparation 2

In a 2.0 liter three-necked flask equipped with a refluxing condenser was introduced 50.0 g of 4-bromophthalic acid and 100.1 g of neopentyl alcohol, to which was slowly added 36 ml of sulfuric acid at 69° C. The mixture was refluxed at a temperature of 115 to 125° C. for 3.5 hours. After cooling, the reaction mixture was moved into a separating funnel containing 600 ml of distilled water. The flask was washed with 500 ml of diethyl ether, and the ether was poured into the separating funnel. After flashing operation, removal of the aqueous layer (lower layer) was repeated 3 times. Then, 250 ml of 5% sodium hydrogen carbonate aqueous solution was added, and after flashing operation made, the aqueous layer showed pH 7 to 8. After removal of the aqueous layer, the organic layer was washed with 300 ml of saturated brine and then with 150 ml of distilled water. After removal of the aqueous layer, the ether layer (upper layer) was placed in an Erlenmeyer flask and dried on anhydrous sodium sulfate. Ether was distilled off under reduced pressure, and the residue was further distilled under reduced pressure. When temperature at the column top reached approximately 170° C., 61.9 g of light yellow viscous liquid was obtained. This was cooled to about −10° C. to give white crystals, which were recrystallized from ethanol to give 33.2 g (39.2% yield) of white crystals in good purity. This white crystalline material was identified in respective analyzers in the same manner as described above. As results, this was confirmed to be dineopentyl 4-bromophthalate. The analytical values are shown in Tables 1 to 3.

Preparation 3

In a 2.0 liter three-necked flask equipped with a refluxing condenser was introduced 24.0 g of 3-fluorophthalic acid and 99.6 g of neopentyl alcohol, to which was slowly added 18 ml of sulfuric acid at 62° C. The mixture was refluxed at a temperature of 115 to 125° C. for 2 hours. After cooling, the reaction mixture was moved into a separating funnel containing 300 ml of distilled water. The flask was washed with 210 ml of diethyl ether, and the ether was poured into the separating funnel. After flashing operation, removal of the aqueous layer (lower layer) was repeated 3 times. Then, 150 ml of 5% sodium hydrogen carbonate aqueous solution was added, and after flashing operation made, the aqueous layer showed pH 7 to 8. After removal of the aqueous layer, the organic layer was washed with 150 ml of saturated brine and then with 150 ml of distilled water. After removal of the aqueous layer, the ether layer (upper layer) was placed in an Erlenmeyer flask and dried on anhydrous sodium sulfate. Ether was distilled off under reduced pressure, and the residue was further distilled under reduced pressure. When temperature at the column top reached approximately 150° C., 15.3 g of yellow viscous liquid was obtained. This was crystallized from ethanol to give 12.0 g (28.4% yield) of white crystals in good purity. This white crystalline material was identified in respective analyzers in the same manner as described above. As results, this was confirmed to be dineopentyl 3-fluorophthalate. The analytical values are shown in Tables 1 to 3.

Preparation 4

In a 2.0 liter three-necked flask equipped with a refluxing condenser was introduced 21.1 g of 4,5-dimethylphthalic acid and 99.7 g of neopentyl alcohol, to which was slowly added 18 ml of sulfuric acid at 67° C. The mixture was refluxed at a temperature of 115 to 125° C. for 2 hours. After cooling, the reaction mixture was moved into a separating funnel containing 300 ml of distilled water. The flask was washed with 210 ml of ethyl ether, and the ether was poured into the separating funnel. After flashing operation, removal of the aqueous layer (lower layer) was repeated 3 times. Then, 150 ml of 5% sodium hydrogen carbonate aqueous solution was added, and after flashing operation made, the aqueous layer showed pH 7 to 8. After removal of the aqueous layer, the organic layer was washed with 150 ml of saturated brine and then with 100 ml of distilled water. After removal of the aqueous layer, the ether layer (upper layer) was placed in an Erlenmeyer flask and dried on anhydrous sodium sulfate. Ether was distilled off under reduced pressure, and the residue was further distilled under reduced pressure. When temperature at the column top reached approximately 170° C., 18.9 g of yellow viscous liquid was obtained. This was crystallized from ethanol to give 12.1 g (36.7% yield) of white crystals in good purity. This white crystalline material was identified in respective analyzers in the same manner as described above. As results, this was confirmed to be dineopentyl 4,5-dimethyl-phthalate. The analytical values are shown in Tables 1 to 3.

Preparation 5

In a 2.0 liter three-necked flask equipped with are fluxing condenser was introduced 32.6 g of 4-tert-butylphthalic acid and 150.0 g of neopentyl alcohol, to which was slowly added 36 ml of sulfuric acid at 66° C. The mixture was refluxed at a temperature of 115 to 125° C. for 3 hours. After cooling, the reaction mixture was moved into a separating funnel containing 400 ml of distilled water. The flask was washed with 300 ml of diethyl ether, and the ether was poured into the separating funnel. After flashing operation, removal of the aqueous layer (lower layer) was repeated 3 times. Then, 200 ml of 5% sodium hydrogen carbonate aqueous solution was added, and after flashing operation made, the aqueous layer showed pH 7 to 8. After removal of the aqueous layer, the organic layer was washed with 200 ml of saturated brine and then with 150 ml of distilled water. After removal of the aqueous layer, the ether layer (upper layer) was placed in an Erlenmeyer flask and dried on anhydrous sodium sulfate. Ether was distilled off under reduced pressure, and the residue was further distilled under reduced pressure. When temperature at the column top reached approximately 170° C., 23.6 g (44.3% yield) of yellow viscous liquid was obtained. This yellow liquid material was identified in respective analyzers in the same manner as described above. As results, this was confirmed to be dineopentyl 4-tert-butylphthalate. The analytical values are shown in Tables 1 to 3.

Preparation 6

In a 2.0 liter three-necked flask equipped with a refluxing condenser was introduced 25.0 g of 4-methylphthalic acid and 100.0 g of n-butyl alcohol, to which was slowly added 18 ml of sulfuric acid at 66° C. The mixture was refluxed at a temperature of 115 to 125° C. for 2 hours. After cooling, the reaction mixture was moved into a separating funnel containing 150 ml of distilled water. The flask was washed with 200 ml of ethyl ether, and the ether was poured into the separating funnel. After flashing operation, removal of the aqueous layer (lower layer) was repeated 3 times. Then, 150 ml of 5% sodium hydrogen carbonate aqueous solution was added, and after flashing operation made, the aqueous layer showed pH 7 to 8. After removal of the aqueous layer, the organic layer was washed with 300 ml of saturated brine and then with 150 ml of distilled water. After removal of the aqueous layer, the ether layer (upper layer) was placed in an Erlenmeyer flask and dried on anhydrous sodium sulfate. Ether was distilled off under reduced pressure, and the residue was further distilled under reduced pressure. When temperature at the column top reached approximately 190° C., 13.0 g of yellow viscous liquid was obtained. This was cooled to approximately −10° C. to give white crystals, which were further recrystallized from ethanol to give 11.8 g (26.5% yield) of white crystals in good purity. This white crystalline material was analyzed by means of MS, $^1$H-NMR and Raman spectra in respective analyzers as described below. As results, this was confirmed to be di-n-butyl 4-methylphthalate. The identification results are shown in Tables 1 to 3.

Preparation 7

In a 2.0 liter three-necked flask equipped with a refluxing condenser was introduced 50.0 g of 4-bromophthalic acid and 100.1 g of n-butyl alcohol, to which was slowly added 36 ml of sulfuric acid at 69° C. The mixture was refluxed at a temperature of 115 to 125° C. for 3.5 hours. After cooling, the reaction mixture was moved into a separating funnel containing 600 ml of distilled water. The flask was washed with 500 ml of diethyl ether, and the ether was poured into the separating funnel. After flashing operation, removal of the aqueous layer (lower layer) was repeated 3 times. Then, 250 ml of 5% sodium hydrogen carbonate aqueous solution was added, and after flashing operation made, the aqueous layer showed pH 7 to 8. After removal of the aqueous layer, the organic layer was washed with 300 ml of saturated brine and then with 150 ml of distilled water. After removal of the aqueous layer, the ether layer (upper layer) was placed in an Erlenmeyer flask and dried on anhydrous sodium sulfate. Ether was distilled off under reduced pressure, and the residue was further distilled under reduced pressure. When temperature at the column top reached approximately 170° C., 61.9 g of light yellow viscous liquid was obtained. This was cooled to approximately −10° C. to give white crystals, which were further recrystallized from ethanol to give 33.2 g (39.2% yield) of white crystals in good purity. This white crystalline material was identified in respective analyzers in the same manner as described above. As results, this was confirmed to be di-n-butyl 4-bromophthalate. The identification results are shown in Tables 1 to 3.

Preparation 8

In a 2.0 liter three-necked flask equipped with a refluxing condenser was introduced 32.6 g of 4-tert-butylphthalic acid and 100.0 g of n-butyl alcohol, to which was slowly added 36 ml of sulfuric acid at 66° C. The mixture was refluxed at a temperature of 115 to 125° C. for 3 hours. After cooling, the reaction mixture was moved into a separating funnel containing 400 ml of distilled water. The flask was washed with 300 ml of diethyl ether, and the ether was poured into the separating funnel. After flashing operation, removal of the aqueous layer (lower layer) was repeated 3 times. Then, 200 ml of 5% sodium hydrogen carbonate aqueous solution was added, and after flashing operation made, the aqueous layer showed pH 7 to 8. After removal of the aqueous layer, the organic layer was washed with 200 ml of saturated brine and then with 150 ml of distilled water. After removal of the aqueous layer, the ether layer (upper layer) was placed in an Erlenmeyer flask and dried on anhydrous sodium sulfate. Ether was distilled off under reduced pressure, and the residue was further distilled under reduced pressure. When temperature at the column top reached approximately 170° C., 20.5 g (43.3% yield) of yellow viscous liquid was obtained. This yellow liquid was identified in respective analyzers in the same manner as described above. As results, this was confirmed to be di-n-butyl 4-tert-butylphthalate. The analytical values are shown in Tables 1 to 3.

Preparation 9

In a 2.0 liter three-necked flask equipped with a refluxing condenser was introduced 25.0 g of 4-methylphthalic acid and 100.0 g of ethyl alcohol, to which was slowly added 36 ml of sulfuric acid at 66° C. The mixture was refluxed at a temperature of 115 to 125° C. for 3 hours. After cooling, the reaction mixture was moved into a separating funnel containing 400 ml of distilled water. The flask was washed with 300 ml of diethyl ether, and the ether was poured into the separating funnel. After flashing operation, removal of the aqueous layer (lower layer) was repeated 3 times. Then, 200 ml of 5% sodium hydrogen carbonate aqueous solution was added, and after flashing operation made, the aqueous layer showed pH 7 to 8. After removal of the aqueous layer, the organic layer was washed with 200 ml of saturated brine and then with 150 ml of distilled water. After removal of the aqueous layer, the ether layer (upper layer) was placed in an Erlenmeyer flask and dried on anhydrous sodium sulfate. Ether was distilled off under reduced pressure, and the residue was further distilled under reduced pressure. When temperature at the column top reached approximately 170° C., 12.5 g (37.5% yield) of yellow viscous liquid was obtained. This yellow liquid was identified in respective analyzers in the same manner as described above. As results, this was confirmed to be diethyl 4-methylphthalate. The analytical values are shown in Tables 1 to 3.

Preparation 10

In a 2.0 liter three-necked flask equipped with are fluxing condenser was introduced 32.6 g of 4-tert-butylphthalic acid and 100.0 g of ethyl alcohol, to which was slowly added 36 ml of sulfuric acid at 66° C. The mixture was refluxed at a temperature of 115 to 125° C. for 3 hours. After cooling, the reaction mixture was moved into a separating funnel containing 400 ml of distilled water. The flask was washed with 300 ml of diethyl ether, and the ether was poured into the separating funnel. After flashing operation, removal of the aqueous layer (lower layer) was repeated 3 times. Then, 200 ml of 5% sodium hydrogen carbonate aqueous solution was added, and after flashing operation made, the aqueous layer showed pH 7 to 8. After removal of the aqueous layer, the organic layer was washed with 200 ml of saturated brine and then with 150 ml of distilled water. After removal of the aqueous layer, the ether layer (upper layer) was placed in an Erlenmeyer flask and dried on anhydrous sodium sulfate. Ether was distilled off under reduced pressure, and the residue was further distilled under reduced pressure. When temperature at the column top reached approximately 170° C., 18.5 g (45.3% yield) of yellow viscous liquid was obtained. This yellow liquid was identified in respective analyzers in the same manner as described above. As results, this was confirmed to be diethyl 4-tert-butylphthalate. The analytical values are shown in Tables 1 to 3.

Preparation 11

In a 2.0 liter three-necked flask equipped with are fluxing condenser was introduced 30.0 g of 4-chlorophthalic acid and 100.0 g of n-butyl alcohol, to which was slowly added 36 ml of sulfuric acid at 66° C. The mixture was refluxed at a temperature of 115 to 125° C. for 3 hours. After cooling, the reaction mixture was moved into a separating funnel containing 400 ml of distilled water. The flask was washed with 300 ml of diethyl ether, and the ether was poured into the separating funnel. After flashing operation, removal of the aqueous layer (lower layer) was repeated 3 times. Then, 200 ml of 5% sodium hydrogen carbonate aqueous solution was added, and after flashing operation made, the aqueous layer showed pH 7 to 8. After removal of the aqueous layer, the organic layer was washed with 200 ml of saturated brine and then with 150 ml of distilled water. After removal of the aqueous layer, the ether layer (upper layer) was placed in an Erlenmeyer flask and dried on anhydrous sodium sulfate. Ether was distilled off under reduced pressure, and the residue was further distilled under reduced pressure. When temperature at the column top reached approximately 170° C., 18.5 g (39.1% yield) of yellow viscous liquid was obtained. This yellow liquid was identified in respective analyzers in the same manner as described above. As results, this was confirmed to be di-n-butyl 4-chlorophthalate. The analytical values are shown in Tables 1 to 3.

Preparation 12

In a 2.0 liter three-necked flask equipped with are fluxing condenser was introduced 33.0 g of 4,5-dichlorophthalic acid and 100.0 g of n-butyl alcohol, to which was slowly added 36 ml of sulfuric acid at 66° C. The mixture was refluxed at a temperature of 115 to 125° C. for 3 hours. After cooling, the reaction mixture was moved into a separating funnel containing 400 ml of distilled water. The flask was washed with 300 ml of diethyl ether, and the ether was poured into the separating funnel. After flashing operation, removal of the aqueous layer (lower layer) was repeated 3 times. Then, 200 ml of 5% sodium hydrogen carbonate aqueous solution was added, and after flashing operation made, the aqueous layer showed pH 7 to 8. After removal of the aqueous layer, the organic layer was washed with 200 ml of saturated brine and then with 150 ml of distilled water. After removal of the aqueous layer, the ether layer (upper layer) was placed in an Erlenmeyer flask and dried on anhydrous sodium sulfate. Ether was distilled off under reduced pressure, and the residue was further distilled under reduced pressure. When temperature at the column top reached approximately 170° C., 16.3 g (33.0% yield) of yellow viscous liquid was obtained. This yellow liquid was identified in respective analyzers in the same manner as described above. As results, this was confirmed to be di-n-butyl 4,5-dichlorophthalate. The analytical values are shown in Tables 1 to 3.

Preparation 13

In a 2.0 liter three-necked flask equipped with are fluxing condenser was introduced 50.0 g of 4-bromophthalic acid and 100.0 g of isohexyl alcohol, to which was slowly added 36 ml of sulfuric acid at 66° C. The mixture was refluxed at a temperature of 115 to 125° C. for 3 hours. After cooling, the reaction mixture was moved into a separating funnel containing 400 ml of distilled water. The flask was washed with 300 ml of diethyl ether, and the ether was poured into the separating funnel. After flashing operation, removal of the aqueous layer (lower layer) was repeated 3 times. Then, 200 ml of 5% sodium hydrogen carbonate aqueous solution was added, and after flashing operation made, the aqueous layer showed pH 7 to 8. After removal of the aqueous layer, the organic layer was washed with 200 ml of saturated brine and then with 150 ml of distilled water. After removal of the aqueous layer, the ether layer (upper layer) was placed in an Erlenmeyer flask and dried on anhydrous sodium sulfate. Ether was distilled off under reduced pressure, and the residue was further distilled under reduced pressure. When temperature at the column top reached approximately 170° C., 35.5 g (42.1% yield) of yellow viscous liquid was obtained. This yellow liquid was identified in respective analyzers in the same manner as described above. As results, this was confirmed to be diisohexyl 4-bromophthalate. The analytical values are shown in Tables 1 to 3.

TABLE 1

| | | MS (Mw/z) | |
|---|---|---|---|
| Preparation | Compound Name | Molecular peak | Distinct peak |
| 1 | Dineopentyl 4-methylphthalate | 320 | 163 |
| 2 | Dineopentyl 4-bromophthalate | 384, 386 | 184, 182 |
| 3 | Dineopentyl 3-fluorophthalate | 324 | 167 |
| 4 | Dineopentyl 4,5-dimethylphthalate | 334 | 177 |
| 5 | Dineopentyl 4-tert-butylphthalate | 362 | 205 |
| 6 | Di-n-butyl 4-methylphthalate | 292 | 163 |
| 7 | Di-n-butyl 4-bromophthalate | 356, 358 | 227, 229 |
| 8 | Di-n-butyl 4-tert-butylphthalate | 334 | 205 |
| 9 | Diethyl 4-methylphthalate | 236 | 163 |
| 10 | Diethyl 4-tert-butylphthalate | 278 | 205 |
| 11 | Di-n-butyl 4-chlorophthalate | 312 | 183 |
| 12 | Di-n-butyl 4,5-dichlorophthalate | 346, 348 | 217 |
| 13 | Diisohexyl 4-bromophthalate | 412, 414 | 182, 184 |

TABLE 2

| | | $^1$H-NMR (ppm; Int) | | | |
|---|---|---|---|---|---|
| Preparation | Compound Name | CH$_3$ al | CH$_3$ ar | CH$_2$ | Aromatic ring |
| 1 | Dineopentyl 4-methylphthalate | 1.0s: 18.1 | 2.4s: 3.0 | 4.0s: 4.0 | 7.3–7.7m: 3.0 |
| 2 | Dineopentyl 4-bromophthalate | 1.0s: 18.0 | — | 4.0d: 4.0 | 7.6–7.8m: 3.0 |
| 3 | Dineopentyl 3–fluorophthalate | 1.0d: 18.0 | — | 4.0s: 2.0<br>4.1s: 2.0 | 7.3–7.8m: 3.0 |
| 4 | Dineopentyl 4,5-dimethylphthalate | 1.0s: 18.0 | 2.4s: 6.0 | 4.0s: 4.0 | 7.6s: 2.0 |
| 5 | Dineopentyl 4-t-butylphthalate | 1.0d: 18.0<br>1.3s: 9.0 | — | 4.0d: 4.0 | 7.3–7.8m: 3.0 |
| 6 | Di-n-butyl 4-methylphthalate | 1.0t: 6.0 | 2.4s: 3.0 | 1.4q: 4.1<br>1.7m: 4.0<br>4.3m: 4.0 | 7.3–7.8m: 3.0 |
| 7 | Di-n-butyl 4-bromophthalate | 1.0td: 6.1 | — | 1.4q: 4.1<br>1.7m: 4.1<br>4.3td: 4.0 | 7.2–7.8m: 2.9 |
| 8 | Di-n-butyl 4-t-butylphthalate | 1.0t: 6.0<br>1.3s: 9.0 | — | 1.4m: 4.0<br>1.7m: 4.1<br>4.3t: 4.0 | 7.3–7.8m: 3.0 |
| 9 | Diethyl 4-methylphthalate | 1.4t: 6.0 | 2.4s: 3.0 | 4.4q: 4.0 | 7.9s: 3.0 |
| 10 | Diethyl 4-tert-butylphthalate | 1.3s: 9.0<br>1.4t: 6.0 | — | 4.4q: 4.0 | 7.3–7.8m: 3.0 |
| 11 | Di-n-butyl 4-chlorophthalate | 1.0t: 6.0 | — | 1.4m: 4.0<br>1.7m: 4.0<br>4.3t: 4.0 | 7.5–7.8m: 3.0 |
| 12 | Di-n-butyl 4,5-dichlorophthalate | 1.0t: 6.0 | — | 1.4m: 4.0<br>1.7m: 4.0<br>4.3t: 4.0 | 7.9s: 2.0 |
| 13 | Diisohexyl 4-bromophthalate | 0.9d: 12.0 | — | 1.0–1.8m: 2.1<br>1.3m: 4.0<br>1.6m: 3.9<br>3.6t: 4.0 | 7.2–7.8m: 3.0 |

TABLE 3

| | | Raman (cm$^{-1}$) | | | Elemental Analysis (%) Found/Calcd. | | |
|---|---|---|---|---|---|---|---|
| Preparation | Compound Name | C=O | C-Car | Cal-H | C | H | O |
| 1 | Dineopentyl 4-methylphthalate | 1724 | 1612 | 2963<br>2923 | 71.1/71.2 | 8.8/8.8 | 20.0/20.0 |
| 2 | Dineopentyl 4-bromophthalate | 1730 | 1593 | 2962<br>2940 | 56.1/56.1 | 6.2/6.5 | 16.6/16.6 |
| 3 | Dineopentyl 3-fluorophthalate | 1728 | 1610 | 2960<br>2908 | 66.7/66.6 | 8.1/7.8 | 20.2/19.7 |

TABLE 3-continued

| Preparation | Compound Name | Raman (cm$^{-1}$) C=O | C-Car | Cal-H | Elemental Analysis (%) Found/Calcd. C | H | O |
|---|---|---|---|---|---|---|---|
| 4 | Dineopentyl 4,5-dimethylphthalate | 1720 | 1613 | 2965 2927 | 71.8/71.8 | 8.9/9.0 | 19.2/19.1 |
| 5 | Dineopentyl 4-t-butylphthalate | 1724 | 1612 | 2962 2918 | 72.8/72.9 | 9.3/9.5 | 17.8/17.7 |
| 6 | Di-n-butyl 4-methylphthalate | 1722 | 1608 | 2913 2873 | 69.8/69.8 | 8.2/8.2 | 20.7/21.9 |
| 7 | Di-n-butyl 4-bromophthalate | 1724 | 1589 | 2976 2937 | 54.1/53.8 | 5.9/5.9 | 15.7/17.9 |
| 8 | Di-n-butyl 4-t-butylphthalate | 1726 | 1606 | 2960 2908 | 71.8/71.8 | 9.0/9.0 | 18.9/19.1 |
| 9 | Diethyl 4-methylphthalate | 1722 | 1610 | 2951 2911 | 66.2/66.1 | 6.7/6.8 | 27.1/27.1 |
| 10 | Diethyl 4-tert-butylphthalate | 1724 | 1606 | 2968 2937 | 68.8/69.0 | 8.1/8.0 | 22.9/23.0 |
| 11 | Di-n-butyl 4-chlorophthalate | 1726 | 1593 | 2935 2907 2910 | 60.9/61.4 | 6.7/6.8 | 19.8/20.5 |
| 12 | Di-n-butyl 4,5-dichlorophthalate | 1730 | 1589 | 2935 2911 2873 | 55.5/55.3 | 5.9/5.8 | 18.2/18.4 |
| 13 | Diisohexyl 4-bromophthalate | 1724 | 1592 | 2971 2940 2871 | 57.9/58.1 | 7.2/7.1 | 19.1/19.3 |

EXAMPLE 1

Preparation of the Solid Catalyst Component (A)

In a 500 ml round bottomed flask equipped with a stirrer, and substituted enough with nitrogen gas, was placed 10 g of diethoxymagnesium and 80 ml of toluene to give a suspension. To this suspension was added 20 ml of titanium tetrachloride, and the mixture was heated up to 80° C. At this point, a solution of 3.5 g of dineopentyl 4-methylphthalate prepared in Preparation 1 in 3.5 ml of toluene was added, and the mixture was further heated up to 110° C. Then, the mixture was kept at 110° C. with stirring for 1 hour. After the reaction completion, the mixture was washed 3 times with 100 ml of toluene at 90° C., and an additional 20 ml of titanium tetrachloride and 80 ml of toluene were added, heated up to 110° C., and stirred for 1 hour. After the reaction completion, the reaction mixture was washed 7 times with 100 ml of n-heptane at 40° C. to yield a solid catalyst component. After solid-liquid separation from the solid catalyst component, the titanium content in the solid portion was determined to be 2.8% by weight.

Formation of a Polymerization Catalyst and Polymerization

Into a 2.0 liter autoclave equipped with a stirrer and substituted completely with nitrogen gas, was loaded 1.32 mmole of triethylaluminum, 0.13 mmole of cyclohexylmethyl-dimethoxysilane and 0.0026 mmole (as titanium atom) of the above solid catalyst component to yield a catalyst for polymerization. Then, 2.0 liter of hydrogen gas and 1.4 liter of liquid propylene were loaded, then pre-polymerized at 20° C. for 5 minutes, and polymerized under heating at 70° C. for 1 hour. The polymerization activity of the solid catalyst component was 60,100 g/g component. The melt index (MI) value of the polymer (a) (measured according to ASTM D 1238 and JIS K 7210) was 19 g/10 min. The polymerization activity for the solid catalyst component used herein was calculated from the following equation: polymerization activity=(a) 270.9 (g)/ 0.00451 (g) of the solid catalyst component.

When this polymer was extracted with boiling n-heptane for 6 hours, the amount of the polymer (b) insoluble in n-heptane was 263.0 g, and the n-heptane-insoluble portion of the polymer was 97.5% by weight. The polymerization activity, heptane-insoluble portion (HI), and melt index (MI) are shown together in Table 4.

EXAMPLE 2

A solution of 3.4 g of dineopentyl phthalate dissolved in 10.2 ml of toluene was used in place of a solution of 3.5 g of dineopentyl 4-methylphthalate dissolved in 3.5 ml of toluene. Otherwise in the same manner as in Example 1, the solid component was prepared and applied to formation of a polymerization catalyst and polymerization. The resulting solid catalyst component contains 3.6% by weight of titanium. The result of polymerization is shown in Table 4.

EXAMPLE 3

A solution of 3.5 g of dineopentyl 3-fluorophthalate prepared in Preparation 3 dissolved in 4.7 ml of toluene was used in place of a solution of 3.5 g of dineopentyl 4-methylphthalate dissolved in 3.5 ml of toluene. Otherwise in the same manner as in Example 1, the solid component was prepared and applied to formation of a polymerization catalyst and polymerization. The resulting solid catalyst component contains 3.2% by weight of titanium. The result of polymerization is shown in Table 4.

EXAMPLE 4

In place of 3.5 g dineopentyl 4-methylphthalate, 3.6 g of dineopentyl 4,5-dimethylphthalate prepared in Preparation 4 was used. Otherwise in the same manner as in Example 1, the solid component was prepared and applied to formation of a polymerization catalyst and polymerization. The resulting solid catalyst component contains 3.6% by weight of titanium. The result of polymerization is shown in Table 4.

EXAMPLE 5

A solution of 4.2 g of dineopentyl 4-bromophthalate prepared in Preparation 2 dissolved in 5.3 ml of toluene was used in place of a solution of 3.5 g of dineopentyl 4-methylphthalate dissolved in 3.5 ml of toluene. Otherwise in the same manner as in Example 1, the solid component was prepared and applied to formation of a polymerization catalyst and polymerization. The resulting solid catalyst component contains 2.9% by weight of titanium. The result of polymerization is shown in Table 4.

EXAMPLE 6

A solution of 3.2 g of tert-butyl neopentyl phthalate dissolved in 9.6 ml of toluene was used in place of a solution of 3.5 g of dineopentyl 4-methylphthalate dissolved in 3.5 ml of toluene. Otherwise in the same manner as in Example 1, the solid component was prepared and applied to formation of a polymerization catalyst and polymerization. The resulting solid catalyst component contains 3.8% by weight of titanium. The result of polymerization is shown in Table 4.

COMPARATIVE EXAMPLE 1

In place of 3.5 g of dineopentyl 4-methylphthalate, 3.0 g of di-n-butylphthalate was used. Otherwise in the same manner as in Example 1, the solid component was prepared and applied to formation of a polymerization catalyst and polymerization. The resulting solid catalyst component contains 3.0% by weight of titanium. The result of polymerization is shown in Table 4.

COMPARATIVE EXAMPLE 2

In place of 3.5 g of dineopentyl 4-methylphthalate, 3.4 g of di-n-pentyl phthalate was used. Otherwise in the same manner as in Example 1, the solid component was prepared and applied to formation of a polymerization catalyst and polymerization. The resulting solid catalyst component contains 2.6% by weight of titanium. The result of polymerization is shown in Table 4.

TABLE 4

| | Polymern. Activity (g-pp/g-cat.) | HI (% by weight) | MI (g/10 min) |
|---|---|---|---|
| Example 1 | 60,100 | 97.5 | 19 |
| Example 2 | 60,600 | 98.6 | 10 |
| Example 3 | 58,000 | 96.9 | 18 |
| Example 4 | 60,900 | 97.3 | 22 |
| Example 5 | 60,800 | 97.1 | 25 |
| Example 6 | 71,300 | 97.2 | 16 |
| Comp. Ex. 1 | 42,400 | 98.7 | 6.6 |
| Comp. Ex. 2 | 46,400 | 97.9 | 10 |

EXAMPLE 7

Preparation of the Solid Catalyst Component (A)

In a 500 ml round bottomed flask equipped with a stirrer, and substituted enough with nitrogen gas, was placed 10 g of diethoxymagnesium and 80 ml of toluene to give a suspension. To this suspension was added 20 ml of titanium tetrachloride, and the mixture was heated up to 80° C. At this point, 3.2 g of di-n-butyl 4-methylphthalate prepared in Preparation 6 was added, and the mixture was further heated up to 110° C. Then, the mixture was kept at 110° C. with stirring for 1 hour. After the reaction completion, the mixture was washed 3 times with 100 ml of toluene at 90° C., and an additional 20 ml of titanium tetrachloride and 80 ml of toluene were added, heated up to 110° C., and stirred for 1 hour. After the reaction completion, the reaction mixture was washed 7 times with 100 ml of n-heptane at 40° C. to yield a solid catalyst component. After solid-liquid separation from the solid catalyst component, the titanium content in the solid portion was determined to be 3.2% by weight.

Formation of a Polymerization Catalyst and Polymerization

Polymerization was carried out in the same manner as in Example 1. The results are shown in Table 5.

EXAMPLE 8

In place of 3.2 g of di-n-butyl 4-methylphthalate, 3.7 g of di-n-butyl 4-tert-butylphthalate prepared in Preparation 8 was used. Otherwise in the same manner as in Example 7, the solid component was prepared and applied to formation of a polymerization catalyst and polymerization. The resulting solid catalyst component contains 3.3% by weight of titanium. The result of polymerization is shown together in Table 5.

EXAMPLE 9

In place of 3.2 g of di-n-butyl 4-methylphthalate, 2.5 g of diethyl 4-methylphthalate prepared in Preparation 9 was used. Otherwise in the same manner as in Example 7, the solid component was prepared and applied to formation of a polymerization catalyst and polymerization. The resulting solid catalyst component contains 3.1% by weight of titanium. The result of polymerization is shown together in Table 5.

EXAMPLE 10

In place of 3.2 g of di-n-butyl 4-methylphthalate, 3.0 g of diethyl 4-tert-butylphthalate prepared in Preparation 10 was used. Otherwise in the same manner as in Example 7, the solid component was prepared and applied to formation of a polymerization catalyst and polymerization. The resulting solid catalyst component contains 3.4% by weight of titanium. The result of polymerization is shown together in Table 5.

EXAMPLE 11

In the same manner as in Example 7, the solid component was prepared, and 0.13 mmole of dicyclopentyldimethoxysilane (DCPDMS) as an organosilicon compound was used in place of 0.13 mmole of cyclohexylmethyldimethoxysilane (CMDMS) in formation of the polymerization catalyst. Otherwise in the same manner as in Example 1, the polymerization catalyst was formed and applied to polymerization. The result of polymerization is shown together in Table 5.

EXAMPLE 12

In the same manner as in Example 7, the solid component was prepared, and 0.13 mmole of diisopropyldimethoxysilane (DIPDMS) as an organosilicon compound was used in place of 0.13 mmole of cyclohexylmethyldimethoxysilane (CMDMS) in formation of the polymerization catalyst. Otherwise in the same manner as in Example 1, the polymerization catalyst was formed and applied to polymerization. The result of polymerization is shown together in Table 5.

COMPARATIVE EXAMPLE 3

In the same manner as in Comparative Example 1, the solid component was prepared, and 0.13 mmole of dicyclopentyldi-methoxysilane (DCPDMS) as an organosilicon compound was used in place of 0.13 mmole of cyclohexylmethyldimethoxysilane (CMDMS) in formation of the polymerization catalyst. Otherwise in the same manner as in Comparative Example 1, the polymerization catalyst was formed and applied to polymerization. The result of polymerization is shown together in Table 5.

COMPARATIVE EXAMPLE 4

In the same manner as in Comparative Example 1, the solid component was prepared, and 0.13 mmole of diisopropyldi-methoxysilane (DIPDMS) as an organosilicon compound was used in place of 0.13 mmole of cyclohexylmethyldimethoxysilane (CMDMS) in formation of the polymerization catalyst. Otherwise in the same manner as in Comparative Example 1, the polymerization catalyst was formed and applied to polymerization. The result of polymerization is shown together in Table 5.

TABLE 5

|  | Polymern. Activity (g/g-cat) | HI (% by weight) | MI (g/10 min) | Organosilicon compound |
|---|---|---|---|---|
| Example 7 | 50,300 | 98.6 | 14 | CMDMS |
| Example 8 | 47,200 | 98.0 | 17 | CMDMS |
| Example 9 | 52,000 | 98.9 | 13 | CMDMS |
| Example 10 | 47,900 | 98.3 | 13 | CMDMS |
| Example 11 | 57,100 | 99.1 | 7.0 | DCPDMS |
| Example 12 | 53,200 | 98.9 | 11 | DIPDMS |
| Comp. Ex. 3 | 52,900 | 99.1 | 3.6 | DCPDMS |
| Comp. Ex. 4 | 47,500 | 98.7 | 6.8 | DIPDMS |

EXAMPLE 13
Preparation of the Solid Catalyst Component (A)

In a 500 ml round bottomed flask equipped with a stirrer, and substituted enough with nitrogen gas, was placed 10 g of diethoxymagnesium and 80 ml of toluene to give a suspension. To this suspension was added 20 ml of titanium tetrachloride, and the mixture was heated up to 80° C. At this point, 3.9 g of di-n-butyl 4-bromophthalate prepared in Preparation 7 was added, and the mixture was further heated up to 110° C. Then, the mixture was kept at 110° C. with stirring for 1 hour. After the reaction completion, the mixture was washed 3 times with 100 ml of toluene at 90° C., and an additional 20 ml of titanium tetrachloride and 80 ml of toluene were added, heated up to 110° C., and stirred for 1 hour. After the reaction completion, the reaction mixture was washed 7 times with 100 ml of n-heptane at 40° C. to yield a solid catalyst component. After solid-liquid separation from the solid catalyst component, the titanium content in the solid portion was determined to be 2.6% by weight.
Formation of a Polymerization Catalyst and Polymerization Polymerization was carried out in the same manner as in Example 1. The results are shown in Table 6.

EXAMPLE 14

In place of 3.9 g of di-n-butyl 4-bromophthalate, 3.2 g of di-n-butyl 4-chlorophthalate prepared in Preparation 11 was used. Otherwise in the same manner as in Example 13, the solid component was prepared and applied to formation of a polymerization catalyst and polymerization. The resulting solid catalyst component contains 3.3% by weight of titanium. The result of polymerization is shown together in Table 6.

EXAMPLE 15

In place of 3.9 g of di-n-butyl 4-bromophthalate, 3.8 g of di-n-butyl 4,5-dichlorophthalate prepared in Preparation 12 was used. Otherwise in the same manner as in Example 13, the solid component was prepared and applied to formation of a polymerization catalyst and polymerization. The resulting solid catalyst component contains 3.0% by weight of titanium. The result of polymerization is shown together in Table 6.

EXAMPLE 16

In place of 3.9 g of di-n-butyl 4-bromophthalate, 4.5 g of diisohexyl 4-bromophthalate prepared in Preparation 13 was used. Otherwise in the same manner as in Example 13, the solid component was prepared and applied to formation of a polymerization catalyst and polymerization. The resulting solid catalyst component contains 2.9% by weight of titanium. The result of polymerization is shown together in Table 6.

EXAMPLE 17

In the same manner as in Example 13, the solid component was prepared, and 0.13 mmole of dicyclopentyldimethoxysilane (DCPDMS) as an organosilicon compound was used in place of 0.13 mmole of cyclohexylmethyldimethoxysilane (CMDMS) in formation of the polymerization catalyst. Otherwise in the same manner as in Example 1, the polymerization catalyst was formed and applied to polymerization. The result of polymerization is shown together in Table 6.

EXAMPLE 18

In the same manner as in Example 13, the solid component was prepared, and 0.13 mmole of diisopropyldimethoxysilane (DIPDMS) as an organosilicon compound was used in place of 0.13 mmole of cyclohexylmethyldimethoxysilane (CMDMS) information of the polymerization catalyst. Otherwise in the same manner as in Example 1, the polymerization catalyst was formed and applied to polymerization. The result of polymerization is shown together in Table 6.

TABLE 6

|  | Polymern. Activity (g/g-cat) | HI (% by weight) | MI (g/10 min) | Organosilicon compound |
|---|---|---|---|---|
| Example 13 | 49,800 | 98.5 | 13 | CMDMS |
| Example 14 | 47,200 | 98.2 | 15 | CMDMS |
| Example 15 | 43,900 | 97.9 | 21 | CMDMS |
| Example 16 | 49,400 | 98.0 | 18 | CMDMS |
| Example 17 | 54,400 | 99.0 | 7.5 | DCPDMS |
| Example 18 | 53,500 | 98.8 | 12 | DIPDMS |

From the results as shown in Tables 4, 5 and 6, it is found that the olefin polymers can be produced in very high yield by effecting polymerization of olefins using the solid catalyst component and catalyst of the present invention. It is also found that the responsiveness to hydrogen is very high.

Industrial Applicability

The catalysts for olefin polymerization of the present invention can afford polymers of olefins in very high yield while highly retaining high stereoregularity. They also have a high responsiveness to hydrogen. Accordingly, they can provide all-purpose polyolefins on a low cost and are expected useful in production of copolymers of olefins having highly functional properties.

What is claimed is:

1. A solid catalyst component for polymerization of olefins, which comprises (a) a magnesium compound, (b) titanium tetrachloride, and (c) a derivative of phthalic acid diester of the following general formula (1):

$$(R^1)_n \text{—} \begin{array}{c} \text{—COOR}^2 \\ \text{—COOR}^2 \end{array} \qquad (1)$$

wherein $R^1$ is an alkyl group of 1 to 8 carbon atoms or a halogen atom; $R^2$ and $R^3$ are the same or different, representing an alkyl group of 1 to 12 carbon atoms; the number n of the substituent $R^1$ is 1 or 2, and when n is 2, $R^1$ may be the same or different.

2. A solid catalyst component for polymerization of olefins as claimed in claim 1, wherein said magnesium compound is a dialkoxymagnesium.

3. A solid catalyst component for polymerization of olefins as claimed in claim 1, wherein in said general formula (1), when n is 1, $R^1$ is a methyl group or a tert-butyl group, or when n is 2, at least one of $R^1$ is a methyl group or a tert-butyl group.

4. A solid catalyst component for polymerization of olefins as claimed in claim 1, wherein in said general formula (1), when n is 1 or 2, $R^1$ is a chlorine atom, a bromine atom or a fluorine atom.

5. A solid catalyst component for polymerization of olefins as claimed in claim 1, wherein in said general formula (1), when n is 1 or 2, $R^1$ is substituted at least for the hydrogen atom at the 4 or 5 position of the benzene ring.

6. A solid catalyst component for polymerization of olefins as claimed in claim 1, wherein in said general formula (1), at least one of $R^2$ and $R^3$ is an alkyl group of 4 to 8 carbon atoms having a tertiary carbon atom.

7. A solid catalyst component for polymerization of olefins as claimed in claim 1, wherein in said general formula (1), at least one of $R^2$ and $R^3$ is a neopentyl group, or at least one of $R^2$ and $R^3$ is a tert-butyl group.

8. A solid catalyst component for polymerization of olefins as claimed in claim 1, wherein said derivative of phthalic acid diester is diethyl 4-methylphthalate, diethyl 4-tert-butylphthalate, diethyl 4-bromophthalate, diethyl 4,5-dichlorophthalate, di-n-butyl 4-chlorophthalate, di-n-butyl 4,5-dichlorophthalate, diisohexyl 4-bromophthalate, di-n-butyl 4-methylphthalate, di-n-butyl 4-tert-butylphthalate, diisobutyl 4-methylphthalate, diisobutyl 4-tert-butylphthalate, dineopentyl 4-methylphthalate, dineopentyl 4,5-dimethyl-phthalate, di-n-butyl 4-bromophthalate, diisobutyl 4-bromophthalate, diisobutyl 4,5-dichlorophthalate, dineopentyl 4-bromophthalate, dineopentyl 3-fluorophthalate, dineopentyl 4-tert-butylphthalate, diisooctyl 4-methylphthalate or diisooctyl 4-bromophthalate.

9. A solid catalyst for polymerization of olefins which comprises:

(A) a solid catalyst component for polymerization of olefins as claimed in claim 1;

(B) an organoaluminum compound of the following general formula (2):

$$R^4{}_p AlQ_{3-p} \qquad (2)$$

wherein $R^4$ is an alkyl group of 1 to 4 carbon atoms; Q is a hydrogen atom or a halogen atom; and p is an integer of 0<p≦3; and (C) an organosilicon compound of the following general formula (3):

$$R^5{}_q Si(OR^6)_{4-q} \qquad (3)$$

wherein $R^5$ is the same or different, representing an alkyl group of 1 to 12 carbon atoms, a cycloalkyl group, a phenyl group, a vinyl group, an allyl group, or an aralkyl group; $R^6$ is the same or different, representing an alkyl group of 1 to 4 carbon atoms, a cycloalkyl group, a phenyl group, a vinyl group, an allyl group, or an aralkyl group; and q is an integer of 0≦q≦3.

10. A solid catalyst component for polymerization of olefins, which comprises a dialkoxymagnesium, (b) titanium tetrachloride, and (c) a phthalic acid diester or a derivative thereof of the following general formula (1):

$$(R^1)_n \text{—} \begin{array}{c} \text{—COOR}^2 \\ \text{—COOR}^2 \end{array} \qquad (1)$$

wherein $R^1$ is an alkyl group of 1 to 8 carbon atoms or a halogen atom; $R^2$ and $R^3$ are the same or different, representing an alkyl group of 1 to 12 carbon atoms; the number n of the substituent $R^1$ is 0, 1 or 2, and when n is 2, $R^1$ may be the same or different; provided that when n is 0, $R^2$ and $R^3$ each is an alkyl group of 4 to 8 carbon atoms having a tertiary carbon atom, and which is prepared by suspending said dialkoxymagnesium in an aromatic hydrocarbon solvent which is liquid at ordinary temperature, followed by contact with said component (c) and then with said component (b), or by suspending said dialkoxymagnesium in an aromatic hydrocarbon solvent which is liquid at ordinary temperature, followed by contact with said component (b) and then with said component (c).

11. A solid catalyst for polymerization of olefins which comprises:

(A) a solid catalyst component for polymerization of olefins as claimed in claim 10;

(B) an organoaluminum compound of the following general formula (2):

$$R^4{}_p AlQ_{3-p} \qquad (2)$$

wherein $R^4$ is an alkyl group of 1 to 4 carbon atoms; Q is a hydrogen atom or a halogen atom; and p is an integer of 0<p≦3; and (C) an organosilicon compound of the following general formula (3):

$$R^5{}_q Si(OR^6)_{4-q} \qquad (3)$$

wherein $R^5$ is the same or different, representing an alkyl group of 1 to 12 carbon atoms, a cycloalkyl group, a phenyl group, a vinyl group, an allyl group, or an aralkyl group; $R^6$ is the same or different, representing an alkyl group of 1 to 4 carbon atoms, a cycloalkyl group, a phenyl group, an vinyl group, an allyl group, or an aralkyl group; and q is an integer of 0≦q≦3.

12. A solid catalyst component for polymerization of olefins as claimed in claim 1, wherein the solid catalyst component is prepared by contacting the component (a), the component (b), and the component (c) in the presence of an aromatic hydrocarbon compound which is in a liquid state at ordinary temperature and has a boiling point at approximately 90 to 150° C.

13. A solid catalyst component for polymerization of olefins as claimed in claim 1, wherein $R^1$ is an alkyl group of 1 to 8 carbon atoms or a halogen atom; $R^2$ and $R^3$ are the same or different, representing an alkyl group of 1 to 12 carbon atoms; the number n of the substituent $R^1$ is 1 or 2, and when n is 2, $R^1$ is a halogen atom.

14. A solid catalyst component for polymerization of olefins as claimed in claim 10, wherein said phthalic acid diester is dineopentyl phthalate, tert-butyl neopentyl phthalate or bis(2,2-dimethylhexyl)phthalate.

* * * * *